US007906592B2

(12) United States Patent
Luo

(10) Patent No.: US 7,906,592 B2
(45) Date of Patent: Mar. 15, 2011

(54) POLYMERS FUNCTIONALIZED WITH IMIDE COMPOUNDS CONTAINING A PROTECTED AMINO GROUP

(75) Inventor: Steven Luo, Copley, OH (US)

(73) Assignee: Bridgestone Corporation (JP)

( * ) Notice: Subject to any disclaimer, the term of this patent is extended or adjusted under 35 U.S.C. 154(b) by 431 days.

(21) Appl. No.: 12/167,697

(22) Filed: Jul. 3, 2008

(65) Prior Publication Data

US 2010/0004414 A1    Jan. 7, 2010

(51) Int. Cl.
C08F 136/06 (2006.01)
C08F 236/06 (2006.01)
C08C 19/22 (2006.01)

(52) U.S. Cl. .................. 525/331.9; 525/333.2
(58) Field of Classification Search ............. 525/331.9, 525/333.2
See application file for complete search history.

(56) References Cited

U.S. PATENT DOCUMENTS

| | | | |
|---|---|---|---|
| 1,223,396 A | 4/1917 | Karlsson | |
| 2,227,957 A | 1/1941 | Brasse | |
| 3,297,667 A | 1/1967 | von Dohlen et al. | |
| 3,541,063 A | 11/1970 | Throckmorton et al. | |
| 3,778,418 A * | 12/1973 | Nakayama | 525/253 |
| 3,794,604 A | 2/1974 | Throckmorton et al. | |
| 4,185,042 A | 1/1980 | Verkouw | |
| 4,340,688 A * | 7/1982 | Rossert et al. | 525/256 |
| 4,446,281 A * | 5/1984 | Takamatsu et al. | 525/282 |
| 4,461,883 A | 7/1984 | Takeuchi et al. | |
| 4,751,275 A | 6/1988 | Witte et al. | |
| 4,791,174 A | 12/1988 | Bronstert et al. | |
| 4,906,706 A | 3/1990 | Hattori et al. | |
| 4,990,573 A | 2/1991 | Andreussi et al. | |
| 5,064,910 A | 11/1991 | Hattori et al. | |
| 5,066,729 A | 11/1991 | Stayer et al. | |
| 5,109,907 A | 5/1992 | Stayer et al. | |
| 5,227,431 A | 7/1993 | Lawson et al. | |
| 5,310,798 A | 5/1994 | Lawson et al. | |
| 5,508,333 A | 4/1996 | Shimizu | |
| 5,567,784 A | 10/1996 | Wieder et al. | |
| 5,844,050 A | 12/1998 | Fukahori et al. | |
| 5,866,171 A | 2/1999 | Kata | |
| 5,866,650 A | 2/1999 | Lawson et al. | |
| 5,876,527 A | 3/1999 | Tsuruta et al. | |
| 5,916,961 A | 6/1999 | Hergenrother et al. | |
| 5,931,211 A | 8/1999 | Tamura | |
| 5,971,046 A | 10/1999 | Koch et al. | |

(Continued)

FOREIGN PATENT DOCUMENTS

DE    138 070    10/1979

(Continued)

OTHER PUBLICATIONS

P.O. Tawney, W.J. Wenisch, S. Van Der Burg and D.I. Relyea. Journal of Applied Polymer Science. vol. 8, pp. 2281-2298 (1964).*

(Continued)

*Primary Examiner* — Randy Gulakowski
*Assistant Examiner* — Mike Dollinger
(74) *Attorney, Agent, or Firm* — Meredith E. Hooker; Arthur Reginelli

(57) ABSTRACT

A method for preparing a functionalized polymer, the method comprising the steps of preparing a reactive polymer and reacting the reactive polymer with an imide compound containing a protected amino group.

24 Claims, 4 Drawing Sheets

U.S. PATENT DOCUMENTS

| | | | |
|---|---|---|---|
| 6,117,927 A * | 9/2000 | Toba et al. | 524/261 |
| 6,172,160 B1 | 1/2001 | Nakamura et al. | |
| 6,194,505 B1 | 2/2001 | Sone et al. | |
| 6,197,888 B1 | 3/2001 | Luo | |
| 6,255,416 B1 | 7/2001 | Sone et al. | |
| 6,291,591 B1 | 9/2001 | Luo | |
| 6,303,692 B1 | 10/2001 | Luo | |
| 6,699,813 B2 | 3/2004 | Luo et al. | |
| 6,759,497 B2 | 7/2004 | Grun et al. | |
| 6,838,526 B1 * | 1/2005 | Sone et al. | 525/332.8 |
| 6,897,270 B2 | 5/2005 | Ozawa et al. | |
| 6,977,281 B1 | 12/2005 | Ozawa et al. | |
| 6,992,147 B1 * | 1/2006 | Ozawa et al. | 525/342 |
| 7,008,899 B2 | 3/2006 | Luo et al. | |
| 7,094,849 B2 | 8/2006 | Luo et al. | |
| 7,153,919 B2 | 12/2006 | Hogan et al. | |
| 7,294,680 B2 | 11/2007 | Sone et al. | |
| 7,335,712 B2 | 2/2008 | Yan et al. | |
| 7,351,776 B2 | 4/2008 | Tartamella et al. | |
| 7,700,673 B2 * | 4/2010 | Wang et al. | 524/104 |
| 2006/0004131 A1 | 1/2006 | Ozawa et al. | |
| 2006/0025539 A1 | 2/2006 | Ozawa et al. | |
| 2006/0030677 A1 | 2/2006 | Ozawa et al. | |
| 2006/0264589 A1 | 11/2006 | Yan et al. | |
| 2006/0264590 A1 | 11/2006 | Hogan et al. | |
| 2007/0149689 A1 | 6/2007 | Wang et al. | |
| 2007/0149717 A1 | 6/2007 | Luo et al. | |

FOREIGN PATENT DOCUMENTS

| | | |
|---|---|---|
| EP | 0450876 A2 | 10/1991 |
| EP | 0863165 | 6/2003 |
| GB | 835752 | 5/1960 |
| JP | 05-051406 | 3/1993 |
| JP | 05-059103 | 3/1993 |
| JP | 10-306113 | 11/1998 |
| JP | 11-035633 | 2/1999 |
| WO | 01/34659 | 5/2001 |
| WO | 02/38615 | 5/2002 |

OTHER PUBLICATIONS

Kenji Ueda, Akira Hirao and Seiichi Nakahama. Synthesis of Polymers with Amino End Groups: Reactions of Anionic Living polymer with alpha-halo-omega-aminoalkanes with a Protected Amino Functionality. Macromolecules 1990, 23, 939-945.*

International Application No. PCT/US2009/049187, International Preliminary Report on Patentability dated Dec. 14, 2009.

Z. Shen, J. Ouyang, F. Wang, Z. Hu, F. Yu, and B. Qian, Journal of Polymer Science: Polymer Chemistry Edition, 1980, vol. 18, pp. 3345-3357.

H.L. Hsieh, H.C. Yeh, Rubber Chemistry and Technology, 1985, vol. 58, pp. 117-145.

D.J. Wilson, Journal of Polymer Science, Part A, Polymer Chemistry, 1995, vol. 33, pp. 2505-2513.

R.P. Quirk, A.M. Kells, Polymer International, 2000, vol. 49, pp. 751-756.

I. Hattori et al., "Modification of Neodymium High cis-1,4 Polybutadiene with Tin Compounds", Journal of Elastomers and Plastics, 1991, vol. 23, pp. 135-151.

I. Hattori et al., "Chemical Modification of Neodymium High cis-1,4-Polybutadiene with Styreneoxide", Polymers for Advanced Technologies, vol. 4, pp. 450-456, Published Apr. 1991.

* cited by examiner

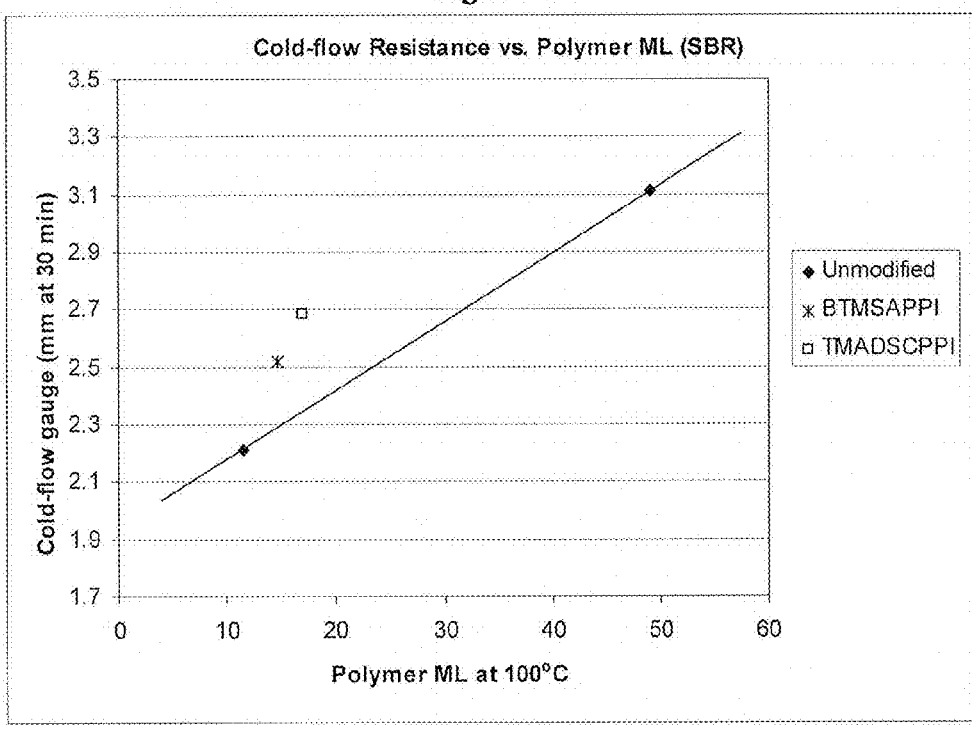

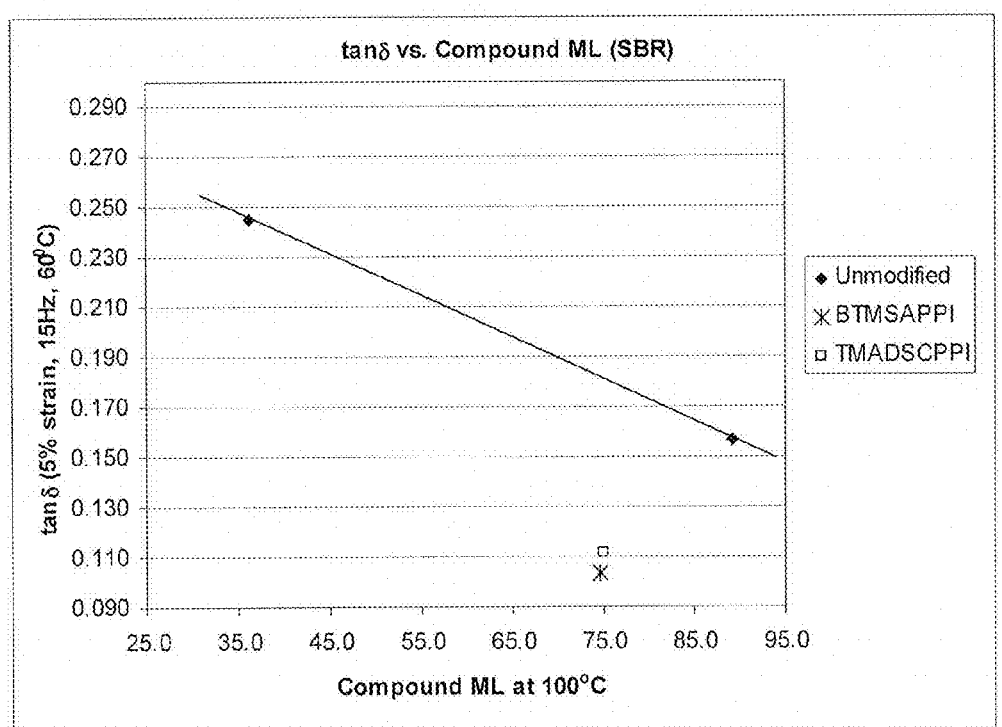

POLYMERS FUNCTIONALIZED WITH IMIDE COMPOUNDS CONTAINING A PROTECTED AMINO GROUP

FIELD OF THE INVENTION

One or more embodiments of the present invention relate to functionalized polymers and methods for their manufacture.

BACKGROUND OF THE INVENTION

In the art of manufacturing tires, it is desirable to employ rubber vulcanizates that demonstrate reduced hysteresis, i.e., less loss of mechanical energy to heat. For example, rubber vulcanizates that show reduced hysteresis are advantageously employed in tire components, such as sidewalls and treads, to yield tires having desirably low rolling resistance. The hysteresis of a rubber vulcanizate is often attributed to the free polymer chain ends within the crosslinked rubber network, as well as the dissociation of filler agglomerates.

Functionalized polymers have been employed to reduce hysteresis of rubber vulcanizates. The functional group of the functionalized polymer may reduce the number of free polymer chain ends via interaction with filler particles. Also, the functional group may reduce filler agglomeration. Nevertheless, whether a particular functional group imparted to a polymer can reduce hysteresis is often unpredictable.

Functionalized polymers may be prepared by post-polymerization treatment of reactive polymers with certain functionalizing agents. However, whether a reactive polymer can be functionalized by treatment with a particular functionalizing agent can be unpredictable. For example, functionalizing agents that work for one type of polymer do not necessarily work for another type of polymer, and vice versa.

Lanthanide-based catalyst systems are known to be useful for polymerizing conjugated diene monomers to form polydienes having a high content of cis-1,4 linkage. The resulting cis-1,4-polydienes may display pseudo-living characteristics in that, upon completion of the polymerization, some of the polymer chains possess reactive ends that can react with certain functionalizing agents to yield functionalized cis-1,4-polydienes.

The cis-1,4-polydienes produced with lanthanide-based catalyst systems typically have a linear backbone, which is believed to provide better tensile properties, higher abrasion resistance, lower hysteresis, and better fatigue resistance as compared to the cis-1,4-polydienes prepared with other catalyst systems such as titanium-, cobalt-, and nickel-based catalyst systems. Therefore, the cis-1,4-polydienes made with lanthanide-based catalysts are particularly suitable for use in tire components such as sidewalls and treads. However, one disadvantage of the cis-1,4-polydienes prepared with lanthanide-based catalysts is that the polymers exhibit high cold flow due to their linear backbone structure. The high cold flow causes problems during storage and transport of the polymers and also hinders the use of automatic feeding equipment in rubber compound mixing facilities.

Anionic initiators are known to be useful for the polymerization of conjugated diene monomers to form polydienes having a combination of 1,2-, cis-1,4- and trans-1,4-linkages. Anionic initiators are also useful for the copolymerization of conjugated diene monomers with vinyl-substituted aromatic compounds. The polymers prepared with anionic initiators may display living characteristics in that, upon completion of the polymerization, the polymer chains possess living ends that are capable of reacting with additional monomers for further chain growth or reacting with certain functionalizing agents to give functionalized polymers. Without the introduction of any coupled or branched structures, the polymers prepared with anionic initiators may also exhibit the problem of high cold flow.

Because functionalized polymers are advantageous, especially in the manufacture of tires, there exists a need to develop new functionalized polymers that give reduced hysteresis and reduced cold flow.

SUMMARY OF THE INVENTION

One or more embodiments of the present invention provide a method for preparing a functionalized polymer, the method comprising the steps of preparing a reactive polymer and reacting the reactive polymer with an imide compound containing a protected amino group.

One or more embodiments of the present invention provide a method for preparing a functional polymer, the method comprising the steps of introducing conjugated diene monomer, optionally monomer copolymerizable therewith, and a catalyst or initiator to form a polymerization mixture and adding an imide compound containing a protected amino group to the polymerization mixture.

One or more embodiments of the present invention provide a method for preparing a polymer, the method comprising the steps of preparing an active polymerization mixture and adding an imide compound containing a protected amino group to the active polymerization mixture.

One or more embodiments of the present invention provide a functionalized polymer prepared by the steps of polymerizing monomer to form a reactive polymer and reacting the reactive polymer with an imide compounds containing a protected amino group.

One or more embodiments of the present invention provide a method for preparing a functionalized polymer, the method comprising the steps of preparing an active polymerization mixture, adding an imide compounds containing a protected amino group to the active polymerization mixture, and adding a co-functionalizing agent to the active polymerization mixture.

One or more embodiments of the present invention provide an imide compound containing a protected amino group.

BRIEF DESCRIPTION OF THE DRAWINGS

FIG. 3 is a graphical plot of cold-flow gauge (mm at 8 min) versus Mooney viscosity (ML 1+4 at 100° C.) for functionalized poly(styrene-co-butadiene) prepared according to one or more embodiments of the present invention as compared to unfunctionalized poly(styrene-co-butadiene).

FIG. 4 is a graphical plot of hysteresis loss (tan δ) versus Mooney viscosity (ML 1+4 at 100° C.) for vulcanizates prepared from functionalized poly(styrene-co-butadiene) prepared according to one or more embodiments of the present invention as compared to vulcanizate prepared from unfunctionalized poly(styrene-co-butadiene).

DETAILED DESCRIPTION OF ILLUSTRATIVE EMBODIMENTS

Figure 1:
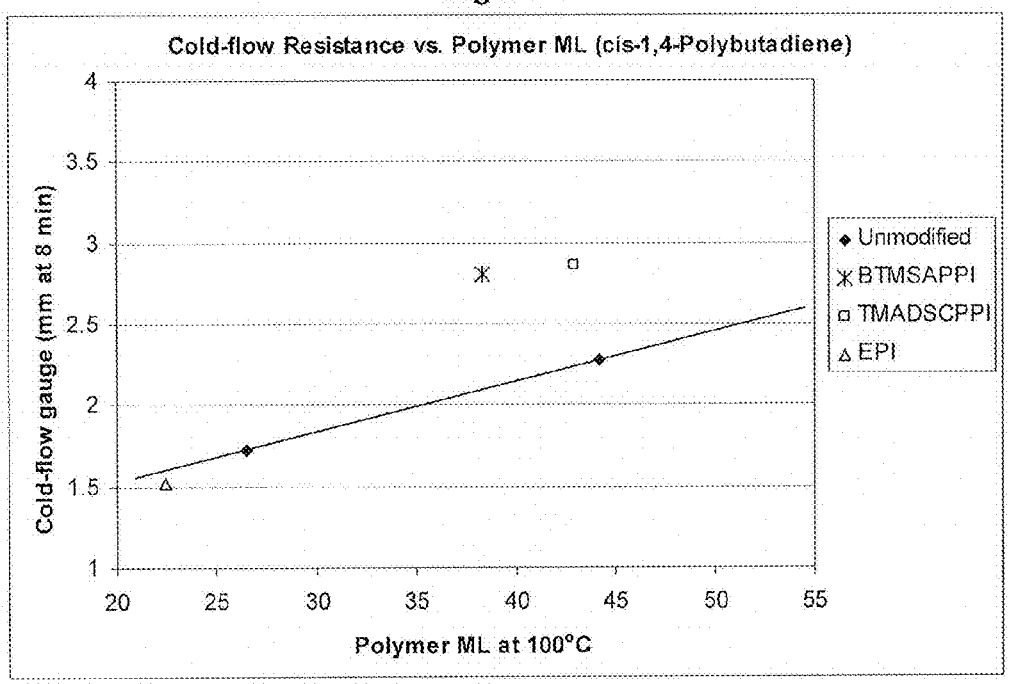
FIG. 1 is a graphical plot of cold-flow gauge (mm at 8 min) versus Mooney viscosity (ML 1+4 at 100° C.) for functionalized cis-1,4-polybutadiene prepared according to one or more embodiments of the present invention as compared to unfunctionalized cis-1,4-polybutadiene.

According to one or more embodiments of the present invention, a reactive polymer is prepared by polymerizing conjugated diene monomer and optionally monomer copolymerizable therewith, and this reactive polymer can then be functionalized by reaction with an imide compound containing a protected amino group. The resultant functionalized polymers can be used in the manufacture of tire components. In one or more embodiments, the resultant functionalized polymers, which include cis-1,4-polydienes and poly(styrene-co-butadiene), exhibit advantageous cold-flow resistance and provide tire components that exhibit advantageously low hysteresis.

Examples of conjugated diene monomer include 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, and 2,4-hexadiene. Mixtures of two or more conjugated dienes may also be utilized in copolymerization.

Examples of monomer copolymerizable with conjugated diene monomer include vinyl-substituted aromatic compounds such as styrene, p-methylstyrene, alpha-methylstyrene, and vinylnaphthalene.

In one or more embodiments, the reactive polymer is prepared by coordination polymerization, wherein monomer is polymerized by using a coordination catalyst system. The key mechanistic features of coordination polymerization have been discussed in books (e.g., Kuran, W., *Principles of Coordination Polymerization*; John Wiley & Sons: New York, 2001) and review articles (e.g., Mulhaupt, R., *Macromolecular Chemistry and Physics* 2003, volume 204, pages 289-327). Coordination catalysts are believed to initiate the polymerization of monomer by a mechanism that involves the coordination or complexation of monomer to an active metal center prior to the insertion of monomer into a growing polymer chain. An advantageous feature of coordination catalysts is their ability to provide stereochemical control of polymerizations and thereby produce stereoregular polymers. As is known in the art, there are numerous methods for creating coordination catalysts, but all methods eventually generate an active intermediate that is capable of coordinating with monomer and inserting monomer into a covalent bond between an active metal center and a growing polymer chain. The coordination polymerization of conjugated dienes is believed to proceed via π-allyl complexes as intermediates. Coordination catalysts can be one-, two-, three- or multi-component systems. In one or more embodiments, a coordination catalyst may be formed by combining a heavy metal compound (e.g., a transition metal compound or a lanthanide compound), an alkylating agent (e.g., an organoaluminum compound), and optionally other co-catalyst components (e.g., a Lewis acid or a Lewis base).

Various procedures can be used to prepare coordination catalysts. In one or more embodiments, a coordination catalyst may be formed in situ by separately adding the catalyst components to the monomer to be polymerized in either a stepwise or simultaneous manner. In other embodiments, a coordination catalyst may be preformed. That is, the catalyst components are pre-mixed outside the polymerization system either in the absence of any monomer or in the presence of a small amount of monomer. The resulting preformed catalyst composition may be aged, if desired, and then added to the monomer that is to be polymerized.

Useful coordination catalyst systems include lanthanide-based catalyst systems. These catalyst systems may advantageously produce cis-1,4-polydienes that, prior to quenching, have reactive chain ends and may be referred to as pseudo-living polymers. While other coordination catalyst systems may also be employed, lanthanide-based catalysts have been found to be particularly advantageous, and therefore, without limiting the scope of the present invention, will be discussed in greater detail.

The practice of one or more embodiments of the present invention is not limited by the selection of any particular lanthanide-based catalyst. In one or more embodiments, the catalyst composition may include a lanthanide compound, an alkylating agent, and a halogen-containing compound that includes one or more labile halogen atoms. Where the lanthanide compound and/or alkylating agent include one or more labile halogen atoms, the catalyst need not include a separate halogen-containing compound; e.g., the catalyst may simply include a halogenated lanthanide compound and an alkylating agent. In certain embodiments, the alkylating agent may include both an aluminoxane and at least one other organoaluminum compound. In yet other embodiments, a compound containing a non-coordinating anion, or a non-coordinating anion precursor, i.e., a compound that can undergo a chemical reaction to form a non-coordinating anion, may be employed in lieu of a halogen-containing compound. In one embodiment, where the alkylating agent includes an organoaluminum hydride compound, the halogen-containing compound may be a tin halide as disclosed in U.S. Pat. No. 7,008,899, which is incorporated herein by reference. In these or other embodiments, other organometallic compounds, Lewis bases, and/or catalyst modifiers may be employed in addition to the ingredients or components set forth above. For example, in one embodiment, a nickel-containing compound may be employed as a molecular weight regulator as disclosed in U.S. Pat. No. 6,699,813, which is incorporated herein by reference.

Various lanthanide compounds or mixtures thereof can be employed. In one or more embodiments, these compounds may be soluble in hydrocarbon solvents such as aromatic hydrocarbons, aliphatic hydrocarbons, or cycloaliphatic hydrocarbons. In other embodiments, hydrocarbon-insoluble lanthanide compounds, which can be suspended in the polymerization medium to form the catalytically active species, are also useful.

Lanthanide compounds may include at least one atom of lanthanum, neodymium, cerium, praseodymium, promethium, samarium, europium, gadolinium, terbium, dysprosium, holmium, erbium, thulium, ytterbium, lutetium, and didymium. Didymium may include a commercial mixture of rare-earth elements obtained from monazite sand.

The lanthanide atom in the lanthanide compounds can be in various oxidation states including but not limited to the 0, +2, +3, and +4 oxidation states. Lanthanide compounds include, but are not limited to, lanthanide carboxylates, lanthanide organophosphates, lanthanide organophosphonates, lanthanide organophosphinates, lanthanide carbamates, lanthanide dithiocarbamates, lanthanide xanthates, lanthanide β-diketonates, lanthanide alkoxides or aryloxides, lanthanide halides, lanthanide pseudo-halides, lanthanide oxyhalides, and organolanthanide compounds.

Without wishing to limit the practice of the present invention, further discussion will focus on neodymium compounds, although those skilled in the art will be able to select similar compounds that are based upon other lanthanide metals.

Neodymium carboxylates include neodymium formate, neodymium acetate, neodymium acrylate, neodymium methacrylate, neodymium valerate, neodymium gluconate, neodymium citrate, neodymium fumarate, neodymium lactate, neodymium maleate, neodymium oxalate, neodymium 2-ethylhexanoate, neodymium neodecanoate (a.k.a. neodymium versatate), neodymium naphthenate, neodymium stearate, neodymium oleate, neodymium benzoate, and neodymium picolinate.

Neodymium organophosphates include neodymium dibutyl phosphate, neodymium dipentyl phosphate, neodymium dihexyl phosphate, neodymium diheptyl phosphate, neodymium dioctyl phosphate, neodymium bis(1-methylheptyl) phosphate, neodymium bis(2-ethylhexyl)phosphate, neodymium didecyl phosphate, neodymium didodecyl phosphate, neodymium dioctadecyl phosphate, neodymium dioleyl phosphate, neodymium diphenyl phosphate, neodymium bis (p-nonylphenyl) phosphate, neodymium butyl (2-ethylhexyl) phosphate, neodymium (1-methylheptyl) (2-ethylhexyl) phosphate, and neodymium (2-ethylhexyl)(p-nonylphenyl) phosphate.

Neodymium organophosphonates include neodymium butyl phosphonate, neodymium pentyl phosphonate, neodymium hexyl phosphonate, neodymium heptyl phosphonate, neodymium octyl phosphonate, neodymium (1-methylheptyl) phosphonate, neodymium (2-ethylhexyl)phosphonate, neodymium decyl phosphonate, neodymium dodecyl phosphonate, neodymium octadecyl phosphonate, neodymium oleyl phosphonate, neodymium phenyl phosphonate, neodymium (p-nonylphenyl) phosphonate, neodymium butyl butylphosphonate, neodymium pentyl pentylphosphonate, neodymium hexyl hexylphosphonate, neodymium heptyl heptylphosphonate, neodymium octyl octylphosphonate, neodymium (1-methylheptyl)(1-methylheptyl)phosphonate, neodymium (2-ethylhexyl)(2-ethylhexyl)phosphonate, neodymium decyl decylphosphonate, neodymium dodecyl dodecylphosphonate, neodymium octadecyl octadecylphosphonate, neodymium oleyl oleylphosphonate, neodymium phenyl phenylphosphonate, neodymium (p-nonylphenyl) (p-nonylphenyl)phosphonate, neodymium butyl (2-ethylhexyl)phosphonate, neodymium (2-ethylhexyl)butylphosphonate, neodymium (1-methylheptyl)(2-ethylhexyl)phosphonate, neodymium (2-ethylhexyl)(1-methylheptyl) phosphonate, neodymium (2-ethylhexyl)(p-nonylphenyl) phosphonate, and neodymium (p-nonylphenyl)(2-ethylhexyl)phosphonate.

Neodymium organophosphinates include neodymium butylphosphinate, neodymium pentylphosphinate, neodymium hexylphosphinate, neodymium heptylphosphinate, neodymium octylphosphinate, neodymium (1-methylheptyl) phosphinate, neodymium (2-ethylhexyl)phosphinate, neodymium decylphosphinate, neodymium dodecylphosphinate, neodymium octadecylphosphinate, neodymium oleylphosphinate, neodymium phenylphosphinate, neodymium (p-nonylphenyl)phosphinate, neodymium dibutylphosphinate, neodymium dipentylphosphinate, neodymium dihexylphosphinate, neodymium diheptylphosphinate, neodymium dioctylphosphinate, neodymium bis(1-methylheptyl)phosphinate, neodymium bis(2-ethylhexyl)phosphinate, neodymium didecylphosphinate, neodymium didodecylphosphinate, neodymium dioctadecylphosphinate, neodymium dioleylphosphinate, neodymium diphenylphosphinate, neodymium bis(p-nonylphenyl)phosphinate, neodymium butyl(2-ethylhexyl)phosphinate, neodymium (1-methylheptyl)(2-ethylhexyl)phosphinate, and neodymium (2-ethylhexyl)(p-nonylphenyl)phosphinate.

Neodymium carbamates include neodymium dimethylcarbamate, neodymium diethylcarbamate, neodymium diisopropylcarbamate, neodymium dibutylcarbamate, and neodymium dibenzylcarbamate.

Neodymium dithiocarbamates include neodymium dimethyldithiocarbamate, neodymium diethyldithiocarbamate, neodymium diisopropyldithiocarbamate, neodymium dibutyldithiocarbamate, and neodymium dibenzyldithiocarbamate.

Neodymium xanthates include neodymium methylxanthate, neodymium ethylxanthate, neodymium isopropylxanthate, neodymium butylxanthate, and neodymium benzylxanthate.

Neodymium β-diketonates include neodymium acetylacetonate, neodymium trifluoroacetylacetonate, neodymium hexafluoroacetylacetonate, neodymium benzoylacetonate, and neodymium 2,2,6,6-tetramethyl-3,5-heptanedionate.

Neodymium alkoxides or aryloxides include neodymium methoxide, neodymium ethoxide, neodymium isopropoxide, neodymium 2-ethylhexoxide, neodymium phenoxide, neodymium nonylphenoxide, and neodymium naphthoxide.

Neodymium halides include neodymium fluoride, neodymium chloride, neodymium bromide, and neodymium iodide. Suitable neodymium pseudo-halides include neodymium cyanide, neodymium cyanate, neodymium thiocyanate, neodymium azide, and neodymium ferrocyanide. Suitable neodymium oxyhalides include neodymium oxyfluoride, neodymium oxychloride, and neodymium oxybromide. Where neodymium halides, neodymium oxyhalides, or other neodymium compounds containing labile halogen atoms are employed, the neodymium-containing compound can also serve as the halogen-containing compound. A Lewis base such as tetrahydrofuran (THF) may be employed as an aid for solubilizing this class of neodymium compounds in inert organic solvents.

The term "organolanthanide compound" may refer to any lanthanide compound containing at least one lanthanide-carbon bond. These compounds are predominantly, though not exclusively, those containing cyclopentadienyl (Cp), substituted cyclopentadienyl, allyl, and substituted allyl ligands. Suitable organolanthanide compounds include $Cp_3Ln$, $Cp_2LnR$, $Cp_2LnCl$, $CpLnCl_2$, $CpLn(cyclooctatetraene)$, $(C_5Me_5)_2LnR$, $LnR_3$, $Ln(allyl)_3$, and $Ln(allyl)_2Cl$, where Ln represents a lanthanide atom, and R represents a hydrocarbyl group.

Various alkylating agents, or mixtures thereof, can be used. Alkylating agents, which may also be referred to as hydrocarbylating agents, include organometallic compounds that can transfer hydrocarbyl groups to another metal. Typically, these agents include organometallic compounds of electropositive metals such as Groups 1, 2, and 3 metals (Groups IA, IIA, and IIIA metals). Where the alkylating agent includes a labile halogen atom, the alkylating agent may also serve as the halogen-containing compound. In one or more embodiments, alkylating agents include organoaluminum and organomagnesium compounds.

The term "organoaluminum compound" may refer to any aluminum compound containing at least one aluminum-carbon bond. In one or more embodiments, organoaluminum compounds may be soluble in a hydrocarbon solvent.

In one or more embodiments, organoaluminum compounds include those represented by the formula $AlR_nX_{3-n}$, where each R, which may be the same or different, is a mono-valent organic group that is attached to the aluminum atom via a carbon atom, where each X, which may be the same or different, is a hydrogen atom, a halogen atom, a carboxylate group, an alkoxide group, or an aryloxide group, and where n is an integer of 1 to 3. In one or more embodiments, mono-valent organic groups may include hydrocarbyl groups or substituted hydrocarbyl groups such as, but not limited to, alkyl, cycloalkyl, alkenyl, cycloalkenyl, aryl, allyl, aralkyl, alkaryl, or alkynyl groups. These groups may contain heteroatoms such as, but not limited to, nitrogen, boron, oxygen, silicon, sulfur, tin, and phosphorus atoms.

Types of organoaluminum compounds represented by the formula $AlR_nX_{3-n}$ include trihydrocarbylaluminum, dihydrocarbylaluminum hydride, hydrocarbylaluminum dihydride, dihydrocarbylaluminum carboxylate, hydrocarbylaluminum bis(carboxylate), dihydrocarbylaluminum alkoxide, hydrocarbylaluminum dialkoxide, dihydrocarbylaluminum halide, hydrocarbylaluminum dihalide, dihydrocarbylaluminum aryloxide, and hydrocarbylaluminum diaryloxide compounds.

Trihydrocarbylaluminum compounds include trimethylaluminum, triethylaluminum, triisobutylaluminum, tri-n-propylaluminum, triisopropylaluminum, tri-n-butylaluminum, tri-t-butylaluminum, tri-n-pentylaluminum, trineopentylaluminum, tri-n-hexylaluminum, tri-n-octylaluminum, tris(2-ethylhexyl)aluminum, tricyclohexylaluminum, tris(1-methylcyclopentyl)aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, and ethyldibenzylaluminum.

Dihydrocarbylaluminum hydride compounds include diethylaluminum hydride, di-n-propylaluminum hydride, diisopropylaluminum hydride, di-n-butylaluminum hydride, diisobutylaluminum hydride, di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride, and benzyl-n-octylaluminum hydride.

Hydrocarbylaluminum dihydride compounds include ethylaluminum dihydride, n-propylaluminum dihydride, isopropylaluminum dihydride, n-butylaluminum dihydride, isobutylaluminum dihydride, and n-octylaluminum dihydride.

Dihydrocarbylaluminum halide compounds include diethylaluminum chloride, di-n-propylaluminum chloride, diisopropylaluminum chloride, di-n-butylaluminum chloride, diisobutylaluminum chloride, di-n-octylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenyl-n-butylaluminum chloride, phenylisobutylaluminum chloride, phenyl-n-octylaluminum chloride, p-tolylethylaluminum chloride, p-tolyl-n-propylaluminum chloride, p-tolylisopropylaluminum chloride, p-tolyl-n-butylaluminum chloride, p-tolylisobutylaluminum chloride, p-tolyl-n-octylaluminum chloride, benzylethylaluminum chloride, benzyl-n-propylaluminum chloride, benzylisopropylaluminum chloride, benzyl-n-butylaluminum chloride, benzylisobutylaluminum chloride, and benzyl-n-octylaluminum chloride.

Hydrocarbylaluminum dihalide compounds include ethylaluminum dichloride, n-propylaluminum dichloride, isopropylaluminum dichloride, n-butylaluminum dichloride, isobutylaluminum dichloride, and n-octylaluminum dichloride.

Other organoaluminum compounds represented by the formula $AlR_nX_{3-n}$ include dimethylaluminum hexanoate, diethylaluminum octoate, diisobutylaluminum 2-ethylhexanoate, dimethylaluminum neodecanoate, diethylaluminum stearate, diisobutylaluminum oleate, methylaluminum bis(hexanoate), ethylaluminum bis(octoate), isobutylaluminum bis(2-ethylhexanoate), methylaluminum bis(neodecanoate), ethylaluminum bis(stearate), isobutylaluminum bis(oleate), dimethylaluminum methoxide, diethylaluminum methoxide, diisobutylaluminum methoxide, dimethylaluminum ethoxide, diethylaluminum ethoxide, diisobutylaluminum ethoxide, dimethylaluminum phenoxide, diethylaluminum phenoxide, diisobutylaluminum phenoxide, methylaluminum dimethoxide, ethylaluminum dimethoxide, isobutylaluminum dimethoxide, methylaluminum diethoxide, ethylaluminum diethoxide, isobutylaluminum diethoxide, methylaluminum diphenoxide, ethylaluminum diphenoxide, and isobutylaluminum diphenoxide.

Another class of organoaluminum compounds include aluminoxanes. Aluminoxanes include oligomeric linear aluminoxanes that can be represented by the general formula:

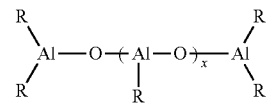

and oligomeric cyclic aluminoxanes that can be represented by the general formula:

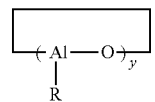

where x may be an integer of 1 to about 100, and in other embodiments about 10 to about 50; y may be an integer of 2 to about 100, and in other embodiments about 3 to about 20; and where each R, which may be the same or different, may be a mono-valent organic group that is attached to the aluminum atom via a carbon atom. Mono-valent organic groups are defined above. It should be noted that the number of moles of the aluminoxane as used in this application refers to the number of moles of the aluminum atoms rather than the number of moles of the oligomeric aluminoxane molecules. This convention is commonly employed in the art of catalysis utilizing aluminoxanes.

Aluminoxanes can be prepared by reacting trihydrocarbylaluminum compounds with water. This reaction can be performed according to known methods, such as (1) a method in which the trihydrocarbylaluminum compound may be dissolved in an organic solvent and then contacted with water, (2) a method in which the trihydrocarbylaluminum compound may be reacted with water of crystallization contained in, for example, metal salts, or water adsorbed in inorganic or organic compounds, and (3) a method in which the trihydrocarbylaluminum compound may be reacted with water in the presence of the monomer or monomer solution that is to be polymerized.

Aluminoxane compounds include methylaluminoxane (MAO), modified methylaluminoxane (MMAO), ethylaluminoxane, n-propylaluminoxane, isopropylaluminoxane, butylaluminoxane, isobutylaluminoxane, n-pentylaluminoxane, neopentylaluminoxane, n-hexylaluminoxane, n-octylaluminoxane, 2-ethylhexylaluminoxane, cyclohexylaluminoxane, 1-methylcyclopentylaluminoxane, phenylaluminoxane, and 2,6-dimethylphenylaluminoxane. Modified methylaluminoxane can be formed by substituting about 20-80% of the methyl groups of methylaluminoxane with $C_2$ to $C_{12}$ hydrocarbyl groups, preferably with isobutyl groups, by using techniques known to those skilled in the art.

Aluminoxanes can be used alone or in combination with other organoaluminum compounds. In one embodiment, methylaluminoxane and at least one other organoaluminum compound (e.g., $AlR_nX_{3-n}$) such as diisobutylaluminum hydride are employed in combination.

The term "organomagnesium compound" may refer to any magnesium compound that contains at least one magnesium-carbon bond. Organomagnesium compounds may be soluble in a hydrocarbon solvent.

One class of organomagnesium compounds that can be utilized may be represented by the formula $MgR_2$, where each R, which may be the same or different, is a mono-valent organic group that is attached to the magnesium atom via a carbon atom. In one or more embodiments, mono-valent organic groups may include hydrocarbyl groups or substituted hydrocarbyl groups such as, but not limited to, alkyl, cycloalkyl, alkenyl, cycloalkenyl, aryl, allyl, aralkyl, alkaryl, or alkynyl groups. These groups may contain heteroatoms such as, but not limited to, nitrogen, boron, oxygen, silicon, sulfur, tin, and phosphorus atoms.

Specific examples of organomagnesium compounds represented by the formula $MgR_2$ include diethylmagnesium, di-n-propylmagnesium, diisopropylmagnesium, dibutylmagnesium, dihexylmagnesium, diphenylmagnesium, and dibenzylmagnesium.

Another class of organomagnesium compounds that can be utilized include those that may be represented by the formula RMgX, where R is a mono-valent organic group that is attached to the magnesium atom via a carbon atom, and X is a hydrogen atom, a halogen atom, a carboxylate group, an alkoxide group, or an aryloxide group. Mono-valent organic groups are defined above. In one or more embodiments, X is a carboxylate group, an alkoxide group, or an aryloxide group.

Exemplary types of organomagnesium compounds represented by the formula RMgX include hydrocarbylmagnesium hydride, hydrocarbylmagnesium halide, hydrocarbylmagnesium carboxylate, hydrocarbylmagnesium alkoxide, and hydrocarbylmagnesium aryloxide.

Specific examples of organomagnesium compounds represented by the formula RMgX include methylmagnesium hydride, ethylmagnesium hydride, butylmagnesium hydride, hexylmagnesium hydride, phenylmagnesium hydride, benzylmagnesium hydride, methylmagnesium chloride, ethylmagnesium chloride, butylmagnesium chloride, hexylmagnesium chloride, phenylmagnesium chloride, benzylmagnesium chloride, methylmagnesium bromide, ethylmagnesium bromide, butylmagnesium bromide, hexylmagnesium bromide, phenylmagnesium bromide, benzylmagnesium bromide, methylmagnesium hexanoate, ethylmagnesium hexanoate, butylmagnesium hexanoate, hexylmagnesium hexanoate, phenylmagnesium hexanoate, benzylmagnesium hexanoate, methylmagnesium ethoxide, ethylmagnesium ethoxide, butylmagnesium ethoxide, hexylmagnesium ethoxide, phenylmagnesium ethoxide, benzylmagnesium ethoxide, methylmagnesium phenoxide, ethylmagnesium phenoxide, butylmagnesium phenoxide, hexylmagnesium phenoxide, phenylmagnesium phenoxide, and benzylmagnesium phenoxide.

Various halogen-containing compounds, or mixtures thereof, that contain one or more labile halogen atoms can be employed. Examples of halogen atoms include, but are not limited to, fluorine, chlorine, bromine, and iodine. A combination of two or more halogen-containing compounds having different halogen atoms can also be utilized. In one or more embodiments, the halogen-containing compound may be soluble in a hydrocarbon solvent. In other embodiments, hydrocarbon-insoluble halogen-containing compounds, which can be suspended in the polymerization medium to form the catalytically active species, may be useful.

Suitable types of halogen-containing compounds include elemental halogens, mixed halogens, hydrogen halides, organic halides, inorganic halides, metallic halides, and organometallic halides.

Elemental halogens include fluorine, chlorine, bromine, and iodine. Mixed halogens include iodine monochloride, iodine monobromide, iodine trichloride, and iodine pentafluoride.

Hydrogen halides include hydrogen fluoride, hydrogen chloride, hydrogen bromide, and hydrogen iodide.

Organic halides include t-butyl chloride, t-butyl bromides, t-butyl iodide, allyl chloride, allyl bromide, allyl iodide, carbon tetrachloride, carbon tetrabromide, carbon tetraiodide, chloroform, bromoform, iodoform, benzyl chloride, benzyl bromide, benzyl iodide, diphenylmethyl chloride, diphenylmethyl bromide, triphenylmethyl chloride, triphenylmethyl bromide, benzylidene chloride, benzylidene bromide, methyltrichlorosilane, phenyltrichlorosilane, dimethyldichlorosilane, diphenyldichlorosilane, trimethylsilyl chloride, trimethylsilyl bromide, trimethylsilyl iodide, benzoyl chloride, benzoyl bromide, propionyl chloride, propionyl bromide, methyl chloroformate, and methyl bromoformate.

Inorganic halides include phosphorus trichloride, phosphorus tribromide, phosphorus triiodide, phosphorus pentachloride, phosphorus oxychloride, phosphorus oxybromide, boron trifluoride, boron trichloride, boron tribromide, silicon tetrafluoride, silicon tetrachloride, silicon tetrabromide, silicon tetraiodide, arsenic trichloride, arsenic tribromide, arsenic triiodide, selenium tetrachloride, selenium tetrabromide, tellurium tetrachloride, tellurium tetrabromide, and tellurium tetraiodide.

Metallic halides include tin tetrachloride, tin tetrabromide, tin tetraiodide, aluminum trichloride, aluminum tribromide, antimony trichloride, antimony pentachloride, antimony tribromide, aluminum triiodide, aluminum trifluoride, gallium trichloride, gallium tribromide, gallium triiodide, gallium trifluoride, indium trichloride, indium tribromide, indium triiodide, indium trifluoride, titanium tetrachloride, titanium tetrabromide, titanium tetraiodide, zinc dichloride, zinc dibromide, zinc diiodide, and zinc difluoride.

Organometallic halides include dimethylaluminum chloride, diethylaluminum chloride, diisobutylaluminum chloride, dimethylaluminum bromide, diethylaluminum bromide, diisobutylaluminum bromide, dimethylaluminum fluoride, diethylaluminum fluoride, diisobutylaluminum fluoride, dimethylaluminum iodide, diethylaluminum iodide, diisobutylaluminum iodide, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride, isobutylaluminum sesquichloride, methylmagnesium chloride, methylmagnesium bromide, methylmagnesium iodide, ethylmagnesium chloride, ethylmagnesium bromide, butylmagnesium chloride, butylmagnesium bromide, phenylmagnesium chloride, phenylmagnesium bromide, benzylmagnesium chloride, trimethyltin chloride, trimethyltin bromide, triethyltin chloride, triethyltin bromide, di-t-butyltin dichloride, di-t-butyltin dibromide, dibutyltin dichloride, dibutyltin dibromide, tributyltin chloride, and tributyltin bromide.

Compounds containing non-coordinating anions are known in the art. In general, non-coordinating anions are sterically bulky anions that do not form coordinate bonds with, for example, the active center of a catalyst system due to steric hindrance. Exemplary non-coordinating anions include tetraarylborate anions and fluorinated tetraarylborate anions. Compounds containing a non-coordinating anion also contain a counter cation such as a carbonium, ammonium, or phosphonium cation. Exemplary counter cations include triarylcarbonium cations and N,N-dialkylanilinium cations. Examples of compounds containing a non-coordinating anion and a counter cation include triphenylcarbonium tetrakis(pentafluorophenyl)borate, N,N-dimethylanilinium tetrakis(pentafluorophenyl)borate, triphenylcarbonium tetrakis[3,5-bis(trifluoromethyl)phenyl]borate, and N,N-dimethylanilinium tetrakis[3,5-bis(trifluoromethyl)phenyl]borate.

Non-coordinating anion precursors include compounds that can form a non-coordinating anion under reaction conditions. Exemplary non-coordinating anion precursors include triarylboron compounds, $BR_3$, where R is a strong electron-withdrawing aryl group such as a pentafluorophenyl or 3,5-bis(trifluoromethyl)phenyl group.

The lanthanide-based catalyst composition used in this invention may be formed by combining or mixing the foregoing catalyst ingredients. Although one or more active catalyst species are believed to result from the combination of the lanthanide-based catalyst ingredients, the degree of interaction or reaction between the various catalyst ingredients or components is not known with any great degree of certainty. Therefore, the term "catalyst composition" has been employed to encompass a simple mixture of the ingredients, a complex of the various ingredients that is caused by physical or chemical forces of attraction, a chemical reaction product of the ingredients, or a combination of the foregoing.

The foregoing lanthanide-based catalyst composition may have high catalytic activity for polymerizing conjugated dienes into cis-1,4-polydienes over a wide range of catalyst concentrations and catalyst ingredient ratios. Several factors may impact the optimum concentration of any one of the catalyst ingredients. For example, because the catalyst ingredients may interact to form an active species, the optimum concentration for any one catalyst ingredient may be dependent upon the concentrations of the other catalyst ingredients.

In one or more embodiments, the molar ratio of the alkylating agent to the lanthanide compound (alkylating agent/Ln) can be varied from about 1:1 to about 1,000:1, in other embodiments from about 2:1 to about 500:1, and in other embodiments from about 5:1 to about 200:1.

In those embodiments where both an aluminoxane and at least one other organoaluminum agent are employed as alkylating agents, the molar ratio of the aluminoxane to the lanthanide compound (aluminoxane/Ln) can be varied from 5:1 to about 1,000:1, in other embodiments from about 10:1 to about 700:1, and in other embodiments from about 20:1 to about 500:1; and the molar ratio of the at least one other organoaluminum compound to the lanthanide compound (Al/Ln) can be varied from about 1:1 to about 200:1, in other embodiments from about 2:1 to about 150:1, and in other embodiments from about 5:1 to about 100:1.

The molar ratio of the halogen-containing compound to the lanthanide compound is best described in terms of the ratio of the moles of halogen atoms in the halogen-containing compound to the moles of lanthanide atoms in the lanthanide compound (halogen/Ln). In one or more embodiments, the halogen/Ln molar ratio can be varied from about 0.5:1 to about 20:1, in other embodiments from about 1:1 to about 10:1, and in other embodiments from about 2:1 to about 6:1.

In yet another embodiment, the molar ratio of the non-coordinating anion or non-coordinating anion precursor to the lanthanide compound (An/Ln) may be from about 0.5:1 to about 20:1, in other embodiments from about 0.75:1 to about 10:1, and in other embodiments from about 1:1 to about 6:1.

The lanthanide-based catalyst composition can be formed by various methods.

In one embodiment, the lanthanide-based catalyst composition may be formed in situ by adding the catalyst ingredients to a solution containing monomer and solvent, or to bulk monomer, in either a stepwise or simultaneous manner. In one embodiment, the alkylating agent can be added first, followed by the lanthanide compound, and then followed by the halogen-containing compound, if used, or by the compound containing a non-coordinating anion or the non-coordinating anion precursor.

In another embodiment, the lanthanide-based catalyst composition may be preformed. That is, the catalyst ingredients are pre-mixed outside the polymerization system either in the absence of any monomer or in the presence of a small amount of at least one conjugated diene monomer at an appropriate temperature, which may be from about $-20°$ C. to about $80°$ C. The amount of conjugated diene monomer that may be used for preforming the catalyst can range from about 1 to about 500 moles, in other embodiments from about 5 to about 250 moles, and in other embodiments from about 10 to about 100 moles per mole of the lanthanide compound. The resulting catalyst composition may be aged, if desired, prior to being added to the monomer that is to be polymerized.

In yet another embodiment, the lanthanide-based catalyst composition may be formed by using a two-stage procedure. The first stage may involve combining the alkylating agent with the lanthanide compound either in the absence of any monomer or in the presence of a small amount of at least one conjugated diene monomer at an appropriate temperature, which may be from about $-20°$ C. to about $80°$ C. The amount of monomer employed in the first stage may be similar to that set forth above for performing the catalyst. In the second stage, the mixture formed in the first stage and the halogen-containing compound, non-coordinating anion, or non-coordinating anion precursor can be charged in either a stepwise or simultaneous manner to the monomer that is to be polymerized.

In one or more embodiments, the reactive polymer is prepared by anionic polymerization, wherein monomer is polymerized by using an anionic initiator. The key mechanistic features of anionic polymerization have been described in books (e.g., Hsieh, H. L.; Quirk, R. P. Anionic Polymerization: Principles and Practical Applications; Marcel Dekker: New York, 1996) and review articles (e.g., Hadjichristidis, N.; Pitsikalis, M.; Pispas, S.; Iatrou, H.; Chem. Rev. 2001, 101 (12), 3747-3792). Anionic initiators may advantageously produce living polymers that, prior to quenching, are capable of reacting with additional monomers for further chain growth or reacting with certain functionalizing agents to give functionalized polymers.

The practice of this invention is not limited by the selection of any particular anionic initiators. In one or more embodiments, the anionic initiator employed is a functional initiator that imparts a functional group at the head of the polymer chain (i.e., the location from which the polymer chain is started). In particular embodiments, the functional group includes one or more heteroatoms (e.g., nitrogen, oxygen, boron, silicon, sulfur, tin, and phosphorus atoms) or heterocyclic groups. In certain embodiments, the functional group reduces the 50° C. hysteresis loss of carbon-black filled vulcanizates prepared from polymers containing the functional group as compared to similar carbon-black filled vulcanizates prepared from polymer that does not include the functional group.

Exemplary anionic initiators include organolithium compounds. In one or more embodiments, organolithium compounds may include heteroatoms. In these or other embodiments, organolithium compounds may include one or more heterocyclic groups.

Types of organolithium compounds include alkyllithium, aryllithium compounds, and cycloalkyllithium compounds. Specific examples of organolithium compounds include ethyllithium, n-propyllithium, isopropyllithium, n-butyllithium, sec-butyllithium, t-butyllithium, n-amyllithium, isoamyllithium, and phenyllithium. Other examples include alkylmagnesium halide compounds such as butylmagnesium bromide and phenylmagnesium bromide. Still other anionic initiators include organosodium compounds such as phenylsodium and 2,4,6-trimethylphenylsodium. Also contemplated are those anionic initiators that give rise to di-living polymers, wherein both ends of a polymer chain is living. Examples of such initiators include dilithio initiators such as those prepared by reacting 1,3-diisopropenylbenzene with sec-butyllithium. These and related difunctional initiators are disclosed in U.S. Pat. No. 3,652,516, which is incorporated herein by reference. Radical anionic initiators may also be employed, including those described in U.S. Pat. No. 5,552,483, which is incorporated herein by reference.

In particular embodiments, the organolithium compounds include a cyclic amine-containing compound such as lithiohexamethyleneimine. These and related useful initiators are disclosed in the U.S. Pat. Nos. 5,332,810, 5,329,005, 5,578,542, 5,393,721, 5,698,646, 5,491,230, 5,521,309, 5,496,940, 5,574,109, and 5,786,441, which are incorporated herein by reference. In other embodiments, the organolithium compounds include alkylthioacetals such as 2-lithio-2-methyl-1,3-dithiane. These and related useful initiators are disclosed in U.S. Publ. Nos. 2006/0030657, 2006/0264590, and 2006/0264589, which are incorporated herein by reference. In still other embodiments, the organolithium compounds include alkoxysilyl-containing initiators, such as lithiated t-butyldimethylpropoxysilane. These and related useful initiators are disclosed in U.S. Publ. No. 2006/0241241, which is incorporated herein by reference.

In one or more embodiments, the anionic initiator employed is trialkyltinlithium compound such as tri-n-butyltinlithium. These and related useful initiators are disclosed in U.S. Pat. Nos. 3,426,006 and 5,268,439, which are incorporated herein by reference.

When elastomeric copolymers containing conjugated diene monomers and vinyl-substituted aromatic monomers are prepared by anionic polymerization, the conjugated diene monomers and vinyl-substituted aromatic monomers may be used at a weight ratio of 95:5 to 50:50, or in other embodiments, 90:10 to 65:35. In order to promote the randomization of comonomers in copolymerization and to control the microstructure (such as 1,2-linkage of conjugated diene monomer) of the polymer, a randomizer, which is typically a polar coordinator, may be employed along with the anionic initiator.

Compounds useful as randomizers include those having an oxygen or nitrogen heteroatom and a non-bonded pair of electrons. Exemplary types of randomizers include linear and cyclic oligomeric oxolanyl alkanes; dialkyl ethers of mono and oligo alkylene glycols (also known as glyme ethers); "crown" ethers; tertiary amines; linear THF oligomers; alkali metal alkoxides; and alkali metal sulfonates. Linear and cyclic oligomeric oxolanyl alkanes are described in U.S. Pat. No. 4,429,091, which is incorporated herein by reference. Specific examples of randomizers include 2,2-bis(2'-tetrahydrofuryl)propane, 1,2-dimethoxyethane, N,N,N',N'-tetramethylethylenediamine (TMEDA), tetrahydrofuran (THF), 1,2-dipiperidylethane, dipiperidylmethane, hexamethylphosphoramide, N-N'-dimethylpiperazine, diazabicyclooctane, dimethyl ether, diethyl ether, tri-n-butylamine, potassium t-amylate, potassium 4-dodecylsulfonate, and mixtures thereof.

The amount of randomizer to be employed may depend on various factors such as the desired microstructure of the polymer, the ratio of monomer to comonomer, the polymerization temperature, as well as the nature of the specific randomizer employed. In one or more embodiments, the amount of randomizer employed may range between 0.05 and 100 moles per mole of the anionic initiator.

The anionic initiator and the randomizer can be introduced to the polymerization system by various methods. In one or more embodiments, the anionic initiator and the randomizer may be added separately to the monomer to be polymerized in either a stepwise or simultaneous manner. In other embodiments, the anionic initiator and the randomizer may be pre-mixed outside the polymerization system either in the absence of any monomer or in the presence of a small amount of monomer, and the resulting mixture may be aged, if desired, and then added to the monomer that is to be polymerized.

In one or more embodiments, regardless of whether a coordination catalyst or an anionic initiator is used to prepared the reactive polymer, a solvent may be employed as a carrier to either dissolve or suspend the catalyst or initiator in order to facilitate the delivery of the catalyst or initiator to the polymerization system. In other embodiments, monomer can be used as the carrier. In yet other embodiments, the catalyst or initiator can be used in their neat state without any solvent.

In one or more embodiments, suitable solvents include those organic compounds that will not undergo polymerization or incorporation into propagating polymer chains during the polymerization of monomer in the presence of the catalyst or initiator. In one or more embodiments, these organic species are liquid at ambient temperature and pressure. In one or more embodiments, these organic solvents are inert to the catalyst or initiator. Exemplary organic solvents include hydrocarbons with a low or relatively low boiling point such as aromatic hydrocarbons, aliphatic hydrocarbons, and cycloaliphatic hydrocarbons. Non-limiting examples of aromatic hydrocarbons include benzene, toluene, xylenes, ethylbenzene, diethylbenzene, and mesitylene. Non-limiting examples of aliphatic hydrocarbons include n-pentane, n-hexane, n-heptane, n-octane, n-nonane, n-decane, isopentane, isohexanes, isopentanes, isooctanes, 2,2-dimethylbutane, petroleum ether, kerosene, and petroleum spirits. And, non-limiting examples of cycloaliphatic hydrocarbons include cyclopentane, cyclohexane, methylcyclopentane, and methylcyclohexane. Mixtures of the above hydrocarbons may also be used. As is known in the art, aliphatic and cycloaliphatic hydrocarbons may be desirably employed for environmental reasons. The low-boiling hydrocarbon solvents are typically separated from the polymer upon completion of the polymerization.

Other examples of organic solvents include high-boiling hydrocarbons of high molecular weights, such as paraffinic oil, aromatic oil, or other hydrocarbon oils that are commonly used to oil-extend polymers. Since these hydrocarbons are non-volatile, they typically do not require separation and remain incorporated in the polymer.

The production of the reactive polymer according to this invention can be accomplished by polymerizing conjugated diene monomer, optionally together with monomer copolymerizable with conjugated diene monomer, in the presence of a catalytically effective amount of a catalyst or an initiator. The introduction of the catalyst or initiator, the conjugated diene monomer, optionally the comonomer, and any solvent if employed forms a polymerization mixture in which the reactive polymer is formed. The amount of the catalyst or initiator to be employed may depend on the interplay of various factors such as the type of catalyst or initiator employed, the purity of the ingredients, the polymerization temperature, the polymerization rate and conversion desired, the molecular weight desired, and many other factors. Accordingly, a specific catalyst or initiator amount cannot be definitively set forth except to say that catalytically effective amounts of the catalyst or initiator may be used.

In one or more embodiments, where a coordination catalyst (e.g., a lanthanide-based catalyst) is employed, the amount of the coordinating metal compound (e.g., a lanthanide compound) used can be varied from about 0.001 to about 2 mmol, in other embodiments from about 0.005 to about 1 mmol, and in still other embodiments from about 0.01 to about 0.2 mmol per 100 gram of monomer.

In other embodiments, where an anionic initiator (e.g., an alkyllithium compound) is employed, the initiator loading may be varied from about 0.05 to about 100 mmol, in other embodiments from about 0.1 to about 50 mmol, and in still other embodiments from about 0.2 to about 5 mmol per 100 gram of monomer.

In one or more embodiments, the polymerization may be carried out in a polymerization system that includes a substantial amount of solvent. In one embodiment, a solution polymerization system may be employed in which both the monomer to be polymerized and the polymer formed are soluble in the solvent. In another embodiment, a precipitation polymerization system may be employed by choosing a solvent in which the polymer formed is insoluble. In both cases, an amount of solvent in addition to the amount of solvent that may be used in preparing the catalyst or initiator is usually added to the polymerization system. The additional solvent may be the same as or different from the solvent used in preparing the catalyst or initiator. Exemplary solvents have been set forth above. In one or more embodiments, the solvent content of the polymerization mixture may be more than 20% by weight, in other embodiments more than 50% by weight, and in still other embodiments more than 80% by weight based on the total weight of the polymerization mixture.

In other embodiments, the polymerization system employed may be generally considered a bulk polymerization system that includes substantially no solvent or a minimal amount of solvent. Those skilled in the art will appreciate the benefits of bulk polymerization processes (i.e., processes where monomer acts as the solvent), and therefore the polymerization system includes less solvent than will deleteriously impact the benefits sought by conducting bulk polymerization. In one or more embodiments, the solvent content of the polymerization mixture may be less than about 20% by weight, in other embodiments less than about 10% by weight, and in still other embodiments less than about 5% by weight based on the total weight of the polymerization mixture. In another embodiment, the polymerization mixture contains no solvents other than those that are inherent to the raw materials employed. In still another embodiment, the polymerization mixture is substantially devoid of solvent, which refers to the absence of that amount of solvent that would otherwise have an appreciable impact on the polymerization process. Polymerization systems that are substantially devoid of solvent may be referred to as including substantially no solvent. In particular embodiments, the polymerization mixture is devoid of solvent.

The polymerization may be conducted in any conventional polymerization vessels known in the art. In one or more embodiments, solution polymerization can be conducted in a conventional stirred-tank reactor. In other embodiments, bulk polymerization can be conducted in a conventional stirred-tank reactor, especially if the monomer conversion is less than about 60%. In still other embodiments, especially where the monomer conversion in a bulk polymerization process is higher than about 60%, which typically results in a highly viscous cement, the bulk polymerization may be conducted in an elongated reactor in which the viscous cement under polymerization is driven to move by piston, or substantially by piston. For example, extruders in which the cement is pushed along by a self-cleaning single-screw or double-screw agitator are suitable for this purpose. Examples of useful bulk polymerization processes are disclosed in U.S. Publication No. 2005/0197474 A1, which is incorporated herein by reference.

In one or more embodiments, all of the ingredients used for the polymerization can be combined within a single vessel (e.g., a conventional stirred-tank reactor), and all steps of the polymerization process can be conducted within this vessel. In other embodiments, two or more of the ingredients can be pre-combined in one vessel and then transferred to another vessel where the polymerization of monomer (or at least a major portion thereof) may be conducted.

The polymerization can be carried out as a batch process, a continuous process, or a semi-continuous process. In the semi-continuous process, the monomer is intermittently charged as needed to replace that monomer already polymerized. In one or more embodiments, the conditions under which the polymerization proceeds may be controlled to maintain the temperature of the polymerization mixture within a range from about −10° C. to about 200° C., in other embodiments from about 0° C. to about 150° C., and in other embodiments from about 20° C. to about 100° C. In one or more embodiments, the heat of polymerization may be removed by external cooling by a thermally controlled reactor jacket, internal cooling by evaporation and condensation of the monomer through the use of a reflux condenser connected to the reactor, or a combination of the two methods. Also, the polymerization conditions may be controlled to conduct the polymerization under a pressure of from about 0.1 atmosphere to about 50 atmospheres, in other embodiments from about 0.5 atmosphere to about 20 atmosphere, and in other embodiments from about 1 atmosphere to about 10 atmospheres. In one or more embodiments, the pressures at which the polymerization may be carried out include those that ensure that the majority of the monomer is in the liquid phase. In these or other embodiments, the polymerization mixture may be maintained under anaerobic conditions.

Regardless of whether the polymerization is catalyzed or initiated by a coordination catalyst system (e.g., a lanthanide-based system) or an anionic initiator (e.g., an alkyllithium initiator), some or all of the resulting polymer chains may possess reactive ends, which are either pseudo-living or living, before the polymerization mixture is quenched. As noted above, the reactive polymer may be referred to as a pseudo-living polymer where a coordination catalyst is employed or as a living polymer where an anionic initiator is employed. In one or more embodiments, a polymerization mixture including reactive polymer may be referred to as an active polymerization mixture. The percentage of polymer chains possessing a reactive end depends on various factors such as the type of catalyst or initiator, the type of monomer, the purity of the ingredients, the polymerization temperature, the monomer conversion, and many other factors. In one or more embodiments, at least about 20% of the polymer chains possess a reactive end, in other embodiments at least about 50% of the polymer chains possess a reactive end, and in still other embodiments at least about 80% of the polymer chains possess a reactive end. In any event, the reactive polymer can be reacted with imide compounds containing a protected amino group to form the functionalized polymer of this invention.

In one or more embodiments, imide compounds containing a protected amino group, which may simply be referred to herein as imide compounds, include those compounds that contain a protected amino group tethered directly or indirectly to an imido group. Protected amino groups include those amino groups that are formed or derived by replacing the two acidic hydrogen atoms of the parent amino group (i.e. —NH$_2$) with substituents such as hydrocarbyl or silyl groups.

Exemplary imido groups include, but are not limited to, phthalimido, maleimido, citraconimido, succinimido, 1,8-naphthalimido, 2,3-naphthalimido, 1,2-cyclopentanedicarboximido, and 1,2-cyclohexanedicarboximido groups. These groups can be defined by the following formulae:

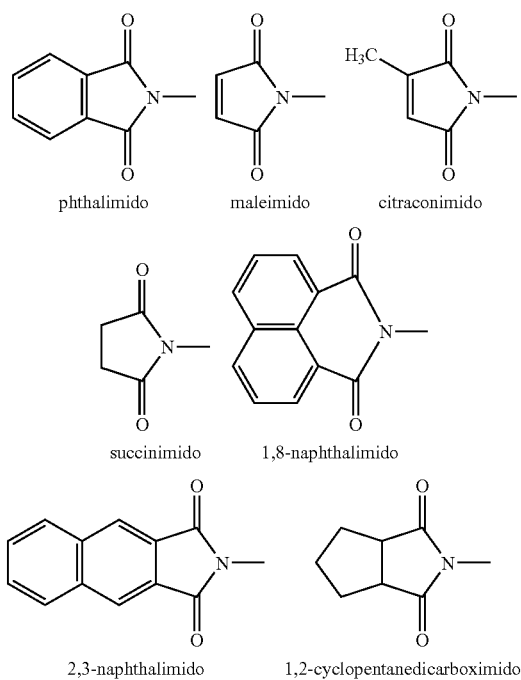

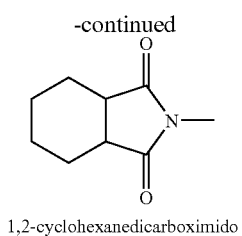

1,2-cyclohexanedicarboximido

Exemplary types of protected amino groups include, but are not limited to, bis(trihydrocarbylsilyl)amino, bis(dihydrocarbylhydrosilyl)amino, 1-aza-disila-1-cyclohydrocarbyl, (trihydrocarbylsilyl)(hydrocarbyl)amino, (dihydrocarbylhydrosilyl)(hydrocarbyl)amino, 1-aza-2-sila-1-cyclohydrocarbyl, dihydrocarbylamino, and 1-aza-1-cyclohydrocarbyl groups.

Specific examples of bis(trihydrocarbylsilyl)amino groups include, but are not limited to, bis(trimethylsilyl)amino, bis(triethylsilyl)amino, bis(triisopropylsilyl)amino, bis(tri-n-propylsilyl)amino, bis(triisobutylsilyl)amino, bis(tri-t-butylsilyl)amino, and bis(triphenylsilyl)amino groups.

Specific examples of bis(dihydrocarbylhydrosilyl)amino groups include, but are not limited to, bis(dimethylhydrosilyl)amino, bis(diethylhydrosilyl)amino, bis(diisopropylhydrosilyl)amino, bis(di-n-propylhydrosilyl)amino, bis(diisobutylhydrosilyl)amino, bis(di-t-butylhydrosilyl)amino, and bis(diphenylhydrosilyl)amino groups.

Specific examples of 1-aza-disila-1-cyclohydrocarbyl groups include, but are not limited to, 2,2,5,5-tetramethyl-1-aza-2,5-disila-1-cyclopentyl, 2,2,5,5-tetraethyl-1-aza-2,5-disila-1-cyclopentyl, 2,2,5,5-tetraphenyl-1-aza-2,5-disila-1-cyclopentyl, 2,2,6,6-tetramethyl-1-aza-2,6-disila-1-cyclohexyl, 2,2,6,6-tetraethyl-1-aza-2,6-disila-1-cyclohexyl, and 2,2,6,6-tetraphenyl-1-aza-2,6-disila-1-cyclohexyl groups.

Specific examples of (trihydrocarbylsilyl)(hydrocarbyl)amino groups include, but are not limited to, (trimethylsilyl)(methyl)amino, (triethylsilyl)(methyl)amino, (triphenylsilyl)(methyl)amino, (trimethylsilyl)(ethyl)amino, (triethylsilyl)(phenyl)amino, and (triisopropylsilyl)(methyl)amino groups.

Specific examples of (dihydrocarbylhydrosilyl)(hydrocarbyl)amino groups include, but are not limited to, (dimethylhydrosilyl)(methyl)amino, (diethylhydrosilyl)(methyl)amino, (diisopropylhydrosilyl)(methyl)amino, (di-n-propylhydrosilyl)(ethyl)amino, (diisobutylhydrosilyl)(phenyl)amino, (di-t-butylhydrosilyl)(phenyl)amino, and (diphenylhydrosilyl)(phenyl)amino groups.

Specific examples of 1-aza-2-sila-1-cyclohydrocarbyl groups include, but are not limited to, 2,2-dimethyl-1-aza-2-sila-1-cyclopentyl, 2,2-diethyl-1-aza-2-sila-1-cyclopentyl, 2,2-diphenyl-1-aza-2-sila-1-cyclopentyl, 2,2-diisopropyl-1-aza-2-sila-1-cyclohexyl, 2,2-dibutyl-1-aza-2-sila-1-cyclohexyl, and 2,2-diphenyl-1-aza-2-sila-1-cyclohexyl groups.

Specific examples of dihydrocarbylamino groups include, but are not limited to, dimethylamino, diethylamino, diphenylamino, diisopropylamino, di-n-butylamino, and dicyclohexylamino groups.

Specific examples of 1-aza-1-cyclohydrocarbyl groups include, but are not limited to, pyrrolidinyl, piperidinyl, homopiperdinyl, 4-methylpiperazinyl, and 4-methylhomopiperazinyl groups.

In one or more embodiments, imide compounds containing a protected amino group may be represented by the formula I:

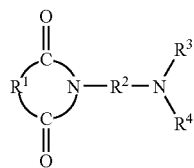

where $R^1$ and $R^2$ are each independently a divalent organic group, and $R^3$ and $R^4$ are each independently a mono-valent organic group or a hydrolyzable group, or $R^3$ and $R^4$ join to form a divalent organic group. In one or more embodiments, the divalent organic group formed by joining $R^3$ and $R^4$ may include one or more hydrolyzable groups. In one or more embodiments, the imide compound may be represented by the formula II

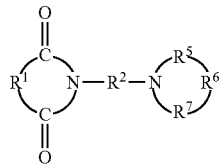

where $R^1$, $R^2$, and $R^6$ are each independently a divalent organic group, and $R^5$ and $R^7$ are each independently a bond or a hydrolyzable group.

In one or more embodiments, mono-valent organic groups may include hydrocarbyl groups or substituted hydrocarbyl groups such as, but not limited to, alkyl, cycloalkyl, alkenyl, cycloalkenyl, aryl, allyl, aralkyl, alkaryl, or alkynyl groups. Substituted hydrocarbyl groups include hydrocarbyl groups in which one or more hydrogen atoms have been replaced by a substituent such as an alkyl group. In one or more embodiments, these groups may include from one, or the appropriate minimum number of carbon atoms to form the group, to 20 carbon atoms. These groups may also contain heteroatoms such as, but not limited to, nitrogen, boron, oxygen, silicon, sulfur, tin, and phosphorus atoms.

In one or more embodiments, hydrolyzable groups include those groups or substituents that are relatively stable, and therefore remain chemically bonded to the nitrogen atom, in non-aqueous environments or environments that are devoid or substantially devoid of water. However, once exposed to water, moisture, or materials containing water or moisture, the hydrolyzable groups or substituents hydrolyze and are thereby cleaved from the nitrogen atom. As a result, the hydrolyzable groups are replaced by a hydrogen atom.

Exemplary hydrolyzable groups include trihydrocarbylsilyl and dihydrocarbylhydrosilyl groups. Specific examples of trihydrocarbylsilyl groups include trimethylsilyl, triethylsilyl, tri-n-propylsilyl, triisopropylsilyl, tri-n-butylsilyl, tri-isobutylsilyl, tri-t-butylsilyl, triphenylsilyl, and t-butyldimethylsilyl groups. Specific examples of dihydrocarbylhydrosilyl groups include dimethylhydrosilyl, diethylhydrosilyl, di-n-propylhydrosilyl, diisopropylhydrosilyl, di-n-butylhydrosilyl, diisobutylhydrosilyl, di-t-butylhydrosilyl, and diphenylhydrosilyl groups. A catalyst may also be used to remove the silyl group from the protected amino group. Suitable catalysts include tetrabutylammonium fluoride, strong acids such as hydrochloric acid, and Lewis Acids such as titanium tetrachloride.

In one or more embodiments, divalent organic groups may include hydrocarbylene groups or substituted hydrocarbylene groups such as, but not limited to, alkylene, cycloalkylene, alkenylene, cycloalkenylene, alkynylene, cycloalkynylene, or arylene groups. Substituted hydrocarbylene groups include hydrocarbylene groups in which one or more hydrogen atoms have been replaced by a substituent such as an alkyl group. In one or more embodiments, these groups may include two, or the appropriate minimum number of carbon atoms to form the group, to 20 carbon atoms. These groups may also contain one or more heteroatoms such as, but not limited to, nitrogen, oxygen, boron, silicon, sulfur, tin, and phosphorus atoms.

In particular embodiments, $R^3$ and $R^4$ of formula I are each independently a silyl group and the imide compound may be represented by the formula III:

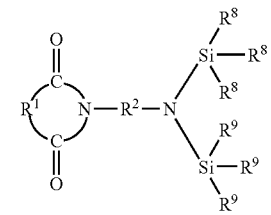

where $R^1$ and $R^2$ are each independently a divalent organic group, and $R^8$ and $R^9$ are each independently a hydrogen atom or a mono-valent organic group, or at least one $R^8$ and at least one $R^9$ join to form a divalent organic group. Where an $R^8$ and an $R^9$ join to form a divalent organic group, the imide compound may be represented by the formula IV:

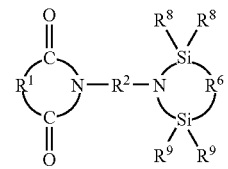

where $R^1$, $R^2$, and $R^6$ are each independently a divalent organic group, and $R^8$ and $R^9$ are each independently a hydrogen atom or a mono-valent organic group.

Exemplary types of imide compounds containing a protected amino group include N-[bis(trihydrocarbylsilyl)aminohydrocarbyl]imide, N-[bis(dihydrocarbylhydrosilyl)aminohydrocarbyl]imide, N-[(1-aza-disila-1-cyclohydrocarbyl)hydrocarbyl]imide, N-[(trihydrocarbylsilyl)(hydrocarbyl)aminohydrocarbyl]imide, N-[(dihydrocarbylhydrosilyl)(hydrocarbyl)aminohydrocarbyl]imide, N-[(1-aza-2-sila-1-cyclohydrocarbyl)hydrocarbyl]imide, N-(dihydrocarbylaminohydrocarbyl)imide, and N-[(1-aza-1-cyclohydrocarbyl)hydrocarbyl]imide.

Specific examples of N-[bis(trihydrocarbylsilyl)aminohydrocarbyl]imide compounds include, but are not limited to, N-[3-bis(trimethylsilyl)amino-1-propyl]phthalimide, N-[3-bis(triethylsilyl)amino-1-propyl]phthalimide, N-[3-bis(triphenylsilyl)amino-1-propyl]phthalimide, N-[2-bis(trimethylsilyl)amino-1-propyl]phthalimide, N-[2-bis(triethylsilyl)amino-1-propyl]phthalimide, N-[2-bis(triphenylsilyl) amino-1-propyl]phthalimide, N-[4-bis(trimethylsilyl) amino-1-butyl]phthalimide, N-[4-bis(triethylsilyl)amino-1-butyl]phthalimide, N-[4-bis(triphenylsilyl)amino-1-butyl] phthalimide, N-[3-bis(trimethylsilyl)amino-1-propyl] maleimide, N-[3-bis(triethylsilyl)amino-1-propyl] maleimide, N-[3-bis(triphenylsilyl)amino-1-propyl] maleimide, N-[3-bis(trimethylsilyl)amino-1-propyl] citraconimide, N-[3-bis(triethylsilyl)amino-1-propyl] citraconimide, N-[3-bis(triphenylsilyl)amino-1-propyl] citraconimide, N-[3-bis(trimethylsilyl)amino-1-propyl] succinimide, N-[3-bis(triethylsilyl)amino-1-propyl] succinimide, N-[3-bis(triphenylsilyl)amino-1-propyl] succinimide, N-[3-bis(trimethylsilyl)amino-1-propyl]-1,8-naphthalimide, N-[3-bis(triethylsilyl)amino-1-propyl]-1,8-naphthalimide, N-[3-bis(triphenylsilyl)amino-1-propyl]-1,8-naphthalimide, N-[3-bis(trimethylsilyl)amino-1-propyl]-2,3-naphthalimide, N-[3-bis(triethylsilyl)amino-1-propyl]-2,3-naphthalimide, N-[3-bis(triphenylsilyl)amino-1-propyl]-2,3-naphthalimide, N-[3-bis(trimethylsilyl)amino-1-propyl]-1,2-cyclopentanedicarboximide, N-[3-bis(triethylsilyl)amino-1-propyl]-1,2-cyclopentanedicarboximide, N-[3-bis(triphenylsilyl)amino-1-propyl]-1,2-cyclopentanedicarboximide, N-[3-bis(trimethylsilyl)amino-1-propyl]-1,2-cyclohexanedicarboximide, N-[3-bis(triethylsilyl)amino-1-propyl]-1,2-cyclohexanedicarboximide, and N-[3-bis(triphenylsilyl)amino-1-propyl]-1,2-cyclohexanedicarboximide.

Specific examples of N-[bis(dihydrocarbylhydrosilyl)aminohydrocarbyl]imide compounds include, but are not limited to, N-[3-bis(dimethylhydrosilyl)amino-1-propyl]phthalimide, N-[3-bis(diphenylhydrosilyl)amino-1-propyl]maleimide, N-[3-bis(dimethylhydrosilyl)amino-1-propyl]citraconimide, N-[3-bis(diphenylhydrosilyl)amino-1-propyl] succinimide, N-[3-bis(diethylhydrosilyl)amino-1-propyl]-1,8-naphthalimide, N-[3-bis(diethylhydrosilyl)amino-1-propyl]-2,3-naphthalimide, N-[3-bis(dimethylhydrosilyl) amino-1-propyl]-1,2-cyclopentanedicarboximide, and N-[3-bis(diethylhydrosilyl)amino-1-propyl]-1,2-cyclohexanedicarboximide.

Specific examples of N-[(1-aza-disila-1-cyclohydrocarbyl)hydrocarbyl]imide compounds include, but are not limited to, N-[3-(2,2,5,5-tetramethyl-1-aza-2,5-disila-1-cyclopentyl)-1-propyl]phthalimide, N-[3-(2,2,5,5-tetraethyl-1-aza-2,5-disila-1-cyclopentyl)-1-propyl]phthalimide, N-[3-(2,2,5,5-tetraphenyl-1-aza-2,5-disila-1-cyclopentyl)-1-propyl]phthalimide, N-[2-(2,2,5,5-tetramethyl-1-aza-2,5-disila-1-cyclopentyl)-1-propyl]phthalimide, N-[2-(2,2,5,5-tetraethyl-1-aza-2,5-disila-1-cyclopentyl)-1-propyl] phthalimide, N-[2-(2,2,5,5-tetraphenyl-1-aza-2,5-disila-1-cyclopentyl)-1-propyl]phthalimide, N-[4-(2,2,5,5-tetramethyl-1-aza-2,5-disila-1-cyclopentyl)-1-butyl] phthalimide, N-[4-(2,2,5,5-tetraethyl-1-aza-2,5-disila-1-cyclopentyl)-1-butyl]phthalimide, N-[4-(2,2,5,5-tetraphenyl-1-aza-2,5-disila-1-cyclopentyl)-1-butyl] phthalimide, N-[3-(2,2,6,6-tetramethyl-1-aza-2,6-disila-1-cyclohexyl)-1-propyl]phthalimide, N-[3-(2,2,6,6-tetraethyl-1-aza-2,6-disila-1-cyclohexyl)-1-propyl]phthalimide, N-[3-(2,2,6,6-tetraphenyl-1-aza-2,6-disila-1-cyclohexyl)-1-propyl]phthalimide, N-[3-(2,2,5,5-tetramethyl-1-aza-2,5-disila-1-cyclopentyl)-1-propyl]maleimide, N-[3-(2,2,5,5-tetraethyl-1-aza-2,5-disila-1-cyclopentyl)-1-propyl] maleimide, N-[3-(2,2,5,5-tetraphenyl-1-aza-2,5-disila-1-cyclopentyl)-1-propyl]maleimide, N-[3-(2,2,5,5-tetramethyl-1-aza-2,5-disila-1-cyclopentyl)-1-propyl] citraconimide, N-[3-(2,2,5,5-tetraethyl-1-aza-2,5-disila-1-cyclopentyl)-1-propyl]citraconimide, N-[3-(2,2,5,5-tetraphenyl-1-aza-2,5-disila-1-cyclopentyl)-1-propyl] citraconimide, N-[3-(2,2,5,5-tetramethyl-1-aza-2,5-disila-1-cyclopentyl)-1-propyl]succinimide, N-[3-(2,2,5,5-tetraethyl-1-aza-2,5-disila-1-cyclopentyl)-1-propyl] succinimide, N-[3-(2,2,5,5-tetraphenyl-1-aza-2,5-disila-1-cyclopentyl)-1-propyl]succinimide, N-[3-(2,2,5,5-tetramethyl-1-aza-2,5-disila-1-cyclopentyl)-1-propyl]-1,8-naphthalimide, N-[3-(2,2,5,5-tetraethyl-1-aza-2,5-disila-1-cyclopentyl)-1-propyl]-1,8-naphthalimide, N-[3-(2,2,5,5-tetraphenyl-1-aza-2,5-disila-1-cyclopentyl)-1-propyl]-1,8-naphthalimide, N-[3-(2,2,5,5-tetramethyl-1-aza-2,5-disila-1-cyclopentyl)-1-propyl]-2,3-naphthalimide, N-[3-(2,2,5,5-tetraethyl-1-aza-2,5-disila-1-cyclopentyl)-1-propyl]-2,3-naphthalimide N-[3-(2,2,5,5-tetraphenyl-1-aza-2,5-disila-1-cyclopentyl)-1-propyl]-2,3-naphthalimide, N-[3-(2,2,5,5-tetramethyl-1-aza-2,5-disila-1-cyclopentyl)-1-propyl]-1,2-cyclopentanedicarboximide, N-[3-(2,2,5,5-tetraethyl-1-aza-2,5-disila-1-cyclopentyl)-1-propyl]-1,2-cyclopentanedicarboximide, N-[3-(2,2,5,5-tetraphenyl-1-aza-2,5-disila-1-cyclopentyl)-1-propyl]-1,2-cyclopentanedicarboximide, N-[3-(2,2,5,5-tetramethyl-1-aza-2,5-disila-1-cyclopentyl)-1-propyl]-1,2-cyclohexanedicarboximide, N-[3-(2,2,5,5-tetraethyl-1-aza-2,5-disila-1-cyclopentyl)-1-propyl]-1,2-cyclohexanedicarboximide, and N-[3-(2,2,5,5-tetraphenyl-1-aza-2,5-disila-1-cyclopentyl)-1-propyl]-1,2-cyclohexanedicarboximide.

Specific examples of N-[(trihydrocarbylsilyl)(hydrocarbyl)aminohydrocarbyl]imide compounds include, but are not limited to, N-[3-(trimethylsilyl)(methyl)amino-1-propyl]phthalimide, N-[3-(triphenylsilyl)(methyl)amino-1-propyl]maleimide, N-[3-(trimethylsilyl)(methyl)amino-1-propyl]citraconimide, N-[3-(triphenylsilyl)(methyl)amino-1-propyl] succinimide, N-[3-(triethylsilyl)(methyl)amino-1-propyl]-1,8-naphthalimide, N-[3-(triethylsilyl)(methyl)amino-1-propyl]-2,3-naphthalimide, N-[3-(trimethylsilyl)(methyl) amino-1-propyl]-1,2-cyclopentanedicarboximide, and N-[3-(triethylsilyl)(methyl)amino-1-propyl]-1,2-cyclohexanedicarboximide.

Specific examples of N-[(dihydrocarbylhydrosilyl)(hydrocarbyl)aminohydrocarbyl]imide compounds include, but are not limited to, N-[3-(dimethylhydrosilyl)(methyl)amino-1-propyl]phthalimide, N-[3-(diphenylhydrosilyl)(methyl) amino-1-propyl]maleimide, N-[3-(dimethylhydrosilyl)(methyl)amino-1-propyl]citraconimide, N-[3-(diphenylhydrosilyl)(methyl)amino-1-propyl]succinimide, N-[3-(diethylhydrosilyl)(methyl)amino-1-propyl]-1,8-naphthalimide, N-[3-(diethylhydrosilyl)(methyl)amino-1-propyl]-2,3-naphthalimide, N-[3-(dimethylhydrosilyl)(methyl)amino-1-propyl]-1,2-cyclopentanedicarboximide, and N-[3-(diethylhydrosilyl)(methyl)amino-1-propyl]-1,2-cyclohexanedicarboximide.

Specific examples of N-[(1-aza-2-sila-1-cyclohydrocarbyl)hydrocarbyl]imide compounds include, but are not limited to, N-[3-(2,2-dimethyl-1-aza-2-sila-1-cyclopentyl)-1-propyl]phthalimide, N-[3-(2,2-diphenyl-1-aza-2-sila-1-cyclopentyl)-1-propyl]maleimide, N-[3-(2,2-dimethyl-1-aza-2-sila-1-cyclopentyl)-1-propyl]citraconimide, N-[3-(2,2-diphenyl-1-aza-2-sila-1-cyclopentyl)-1-propyl] succinimide, N-[3-(2,2-diethyl-1-aza-2-sila-1-cyclopentyl)-1-propyl]-1,8-naphthalimide, N-[3-(2,2-diethyl-1-aza-2-sila-1-cyclopentyl)-1-propyl]-2,3-naphthalimide, N-[3-(2,2-dimethyl-1-aza-2-sila-1-cyclopentyl)-1-propyl]-1,2-cyclopentanedicarboximide, N-[3-(2,2-diethyl-1-aza-2-sila-1-cyclopentyl)-1-propyl]-1,2-cyclohexanedicarboximide, N-[3-(2,2-dimethyl-1-aza-2-sila-1-cyclohexyl)-1-propyl] phthalimide, N-[3-(2,2-diphenyl-1-aza-2-sila-1-cyclohexyl)-1-propyl]maleimide, N-[3-(2,2-dimethyl-1-aza-2-sila-1-cyclohexyl)-1-propyl]citraconimide, N-[3-(2,2-diphenyl-1-aza-2-sila-1-cyclohexyl)-1-propyl]succinimide, N-[3-(2,2-diethyl-1-aza-2-sila-1-cyclohexyl)-1-propyl]-1,8-naphthalimide, N-[3-(2,2-diethyl-1-aza-2-sila-1-cyclo hexyl)-1-propyl]-2,3-naphthalimide, N-[3-(2,2-dimethyl-1-aza-2-sila-1-cyclohexyl)-1-propyl]-1,2-cyclopentanedicarboximide, and N-[3-(2,2-diethyl-1-aza-2-sila-1-cyclohexyl)-1-propyl]-1,2-cyclohexanedicarboximide.

Specific examples of N-(dihydrocarbylaminohydrocarbyl) imide compounds include, but are not limited to, N-(3-dimethylamino-1-propyl)phthalimide, N-(3-diphenylamino-1-propyl)maleimide, N-(3-dimethylamino-1-propyl)citraconimide, N-(3-diphenylamino-1-propyl)succinimide, N-(3-diethylamino-1-propyl)-1,8-naphthalimide, N-(3-diethylamino-1-propyl)-2,3-naphthalimide, N-(3-dimethylamino-1-propyl)-1,2-cyclopentanedicarboximide, and N-(3-diethylamino-1-propyl)-1,2-cyclohexanedicarboximide.

Specific examples of N-[(1-aza-1-cyclohydrocarbyl)hydrocarbyl]imide compounds include, but are not limited to, N-(3-pyrrolidinyl-1-propyl)phthalimide, N-(3-homopiperidinyl-1-propyl)maleimide, N-(3-pyrrolidinyl-1-propyl)citraconimide, N-(3-homopiperdinyl-1-propyl)succinimide, N-(3-piperidinyl-1-propyl)-1,8-naphthalimide, N-(3-piperidinyl-1-propyl)-2,3-naphthalimide, N-(3-pyrrolidinyl-1-propyl)-1,2-cyclopentanedicarboximide, N-(3-piperidinyl-1-propyl)-1,2-cyclohexanedicarboximide, N-[3-(4-methylpiperazinyl)-1-propyl]phthalimide, and N-[3-(4-methylhomopiperazinyl)-1-propyl]phthalimide.

In one or more embodiments, the imide compounds employed in practicing the present invention can be prepared by reacting a metal imide salt such as potassium phthalimide with an organic halide compound containing a protected amino group, by employing techniques similar to those employed in the Gabriel synthesis. This reaction can be conducted in a polar aprotic solvent, such as N,N-dimethylformamide or N,N-dimethylacetamide, to achieve advantageous reaction kinetics.

The amount of the imide compound that can be added to the polymerization mixture may depend on various factors including the type and amount of catalyst or initiator used to initiate the polymerization and the desired degree of functionalization. In one or more embodiments, where the reactive polymer is prepared by employing a lanthanide-based catalyst, the amount of the imide compound employed can be described with reference to the lanthanide metal of the lanthanide compound. For example, the molar ratio of the imide compound to the lanthanide metal may be from about 1:1 to about 200:1, in other embodiments from about 5:1 to about 150:1, and in other embodiments from about 10:1 to about 100:1.

In other embodiments, such as where the reactive polymer is prepared by using an anionic initiator, the amount of the imide compound employed can be described with reference to the amount of metal cation associated with the initiator. For example, where an organolithium initiator is employed, the molar ratio of the imide compound to the lithium cation may be from about 0.3:1 to about 2:1, in other embodiments from about 0.6:1 to about 1.5:1, and in other embodiments from 0.8:1 to about 1.2:1.

In one or more embodiments, in addition to the imide compound, a co-functionalizing agent may also be added to the polymerization mixture to yield a functionalized polymer with tailored properties. A mixture of two or more co-functionalizing agents may also be employed. The co-functionalizing agent may be added to the polymerization mixture prior to, together with, or after the introduction of the imide compound. In one or more embodiments, the co-functionalizing agent is added to the polymerization mixture at least 5 minutes after, in other embodiments at least 10 minutes after, and in other embodiments at least 30 minutes after the introduction of the imide compound.

In one or more embodiments, co-functionalizing agents include compounds or reagents that can react with a reactive polymer produced by this invention and thereby provide the polymer with a functional group that is distinct from a propagating chain that has not been reacted with the co-functionalizing agent. The functional group may be reactive or interactive with other polymer chains (propagating and/or non-propagating) or with other constituents such as reinforcing fillers (e.g. carbon black) that may be combined with the polymer. In one or more embodiments, the reaction between the co-functionalizing agent and the reactive polymer proceeds via an addition or substitution reaction.

Useful co-functionalizing agents may include compounds that simply provide a functional group at the end of a polymer chain without joining two or more polymer chains together, as well as compounds that can couple or join two or more polymer chains together via a functional linkage to form a single macromolecule. The latter type of co-functionalizing agents may also be referred to as coupling agents.

In one or more embodiments, co-functionalizing agents include compounds that will add or impart a heteroatom to the polymer chain. In particular embodiments, co-functionalizing agents include those compounds that will impart a functional group to the polymer chain to form a functionalized polymer that reduces the 50° C. hysteresis loss of a carbon-black filled vulcanizates prepared from the functionalized polymer as compared to similar carbon-black filled vulcanizates prepared from non-functionalized polymer. In one or more embodiments, this reduction in hysteresis loss is at least 5%, in other embodiments at least 10%, and in other embodiments at least 15%.

In one or more embodiments, suitable co-functionalizing agents include those compounds that contain groups that may react with the reactive polymers produced in accordance with this invention. Exemplary co-functionalizing agents include ketones, quinones, aldehydes, amides, esters, isocyanates, isothiocyanates, epoxides, imines, aminoketones, aminothioketones, and acid anhydrides. Examples of these compounds are disclosed in U.S. Pat. Nos. 4,906,706, 4,990,573, 5,064,910, 5,567,784, 5,844,050, 6838,526, 6977,281, and 6,992,147; U.S. Pat. Publication Nos. 2006/0004131 A1, 2006/0025539 A1, 2006/0030677 A1, and 2004/0147694 A1; Japanese Patent Application Nos. 05-051406A, 05-059103A, 10-306113A, and 11-035633A; which are incorporated herein by reference. Other examples of co-functionalizing agents include azine compounds as described in U.S. Ser. No. 11/640,711, hydrobenzamide compounds as disclosed in U.S. Ser. No. 11/710,713, nitro compounds as disclosed in U.S. Ser. No. 11/710,845, and protected oxime compounds as disclosed in U.S. Ser. No. 60/875,484, all of which are incorporated herein by reference.

In particular embodiments, the co-functionalizing agents employed may be metal halides, metalloid halides, alkoxysilanes, metal carboxylates, hydrocarbylmetal carboxylates, hydrocarbylmetal ester-carboxylates, and metal alkoxides.

Exemplary metal halide compounds include tin tetrachloride, tin tetrabromide, tin tetraiodide, n-butyltin trichloride, phenyltin trichloride, di-n-butyltin dichloride, diphenyltin dichloride, tri-n-butyltin chloride, triphenyltin chloride, germanium tetrachloride, germanium tetrabromide, germanium tetraiodide, n-butylgermanium trichloride, di-n-butylgermanium dichloride, and tri-n-butylgermanium chloride.

Exemplary metalloid halide compounds include silicon tetrachloride, silicon tetrabromide, silicon tetraiodide, methyltrichlorosilane, phenyltrichlorosilane, dimethyldichlorosilane, diphenyldichlorosilane, boron trichloride, boron tribromide, boron triiodide, phosphorous trichloride, phosphorous tribromide, and phosphorus triiodide.

In one or more embodiments, the alkoxysilanes may include at least one group selected from the group consisting of an epoxy group and an isocyanate group.

Exemplary alkoxysilane compounds including an epoxy group include (3-glycidyloxypropyl)trimethoxysilane, (3-glycidyloxypropyl)triethoxysilane, (3-glycidyloxypropyl)triphenoxysilane, (3-glycidyloxypropyl)methyldimethoxysilane, (3-glycidyloxypropyl)methyldiethoxysilane, (3-glycidyloxypropyl)methyldiphenoxysilane, [2-(3,4-epoxycyclohexyl)ethyl]trimethoxysilane, and [2-(3,4-epoxycyclohexyl)ethyl]triethoxysilane, Exemplary alkoxysilane compounds including an isocyanate group include (3-isocyanatopropyl)trimethoxysilane, (3-isocyanatopropyl)triethoxysilane, (3-isocyanatopropyl)triphenoxysilane, (3-isocyanatopropyl)methyldimethoxysilane, (3-isocyanatopropyl)methyldiethoxysilane (3-isocyanatopropyl)methyldiphenoxysilane, (isocyanatomethyl)methyldimethoxysilane.

Exemplary metal carboxylate compounds include tin tetraacetate, tin bis(2-ethylhexanaote), and tin bis(neodecanoate).

Exemplary hydrocarbylmetal carboxylate compounds include triphenyltin 2-ethylhexanoate, tri-n-butyltin 2-ethylhexanoate, tri-n-butyltin neodecanoate, triisobutyltin 2-ethylhexanoate, diphenyltin bis(2-ethylhexanoate), di-n-butyltin bis(2-ethylhexanoate), di-n-butyltin bis(neodecanoate), phenyltin tris(2-ethylhexanoate), and n-butylltin tris(2-ethylhexanoate).

Exemplary hydrocarbylmetal ester-carboxylate compounds include di-n-butyltin bis(n-octylmaleate), di-n-octyltin bis(n-octylmaleate), diphenyltin bis(n-octylmaleate), di-n-butyltin bis(2-ethylhexylmaleate), di-n-octyltin bis(2-ethylhexylmaleate), and diphenyltin bis(2-ethylhexylmaleate.

Exemplary metal alkoxide compounds include dimethoxytin, diethoxytin, tetraethoxytin, tetra-n-propoxytin, tetraisopropoxytin, tetra-n-butoxytin, tetraisobutoxytin, tetra-t-butoxytin, and tetraphenoxytin.

The amount of the co-functionalizing agent that can be added to the polymerization mixture may depend on various factors including the type and amount of catalyst or initiator used to initiate the polymerization and the desired degree of functionalization. In one or more embodiments, where the reactive polymer is prepared by employing a lanthanide-based catalyst, the amount of the co-functionalizing agent employed can be described with reference to the lanthanide metal of the lanthanide compound. For example, the molar ratio of the co-functionalizing agent to the lanthanide metal may be from about 1:1 to about 200:1, in other embodiments from about 5:1 to about 150:1, and in other embodiments from about 10:1 to about 100:1.

In other embodiments, such as where the reactive polymer is prepared by using an anionic initiator, the amount of the co-functionalizing agent employed can be described with reference to the amount of metal cation associated with the initiator. For example, where an organolithium initiator is employed, the molar ratio of the co-functionalizing agent to the lithium cation may be from about 0.3:1 to about 2:1, in other embodiments from about 0.6:1 to about 1.5:1, and in other embodiments from 0.8:1 to about 1.2:1.

The amount of the co-functionalizing agent employed can also be described with reference to the imide compound. In one or more embodiments, the molar ratio of the co-functionalizing agent to the imide compound may be from about 0.05:1 to about 1:1, in other embodiments from about 0.1:1 to about 0.8:1, and in other embodiments from about 0.2:1 to about 0.6:1

In one or more embodiments, the imide compound (and optionally the co-functionalizing agent) can be reacted with the reactive polymer after a desired monomer conversion is achieved but before the polymerization mixture is quenched by a quenching agent. In one or more embodiments, the reaction between the imide compound and the reactive polymer may take place within 30 minutes, in other embodiments within 5 minutes, and in other embodiments within one minute after the peak polymerization temperature is reached. In one or more embodiments, the reaction between the imide compound and the reactive polymer can occur once the peak polymerization temperature is reached. In other embodiments, the reaction between the imide compound and the reactive polymer can occur after the reactive polymer has been stored. In one or more embodiments, the storage of the reactive polymer occurs at room temperature or below under an inert atmosphere. In one or more embodiments, the reaction between the imide compound and the reactive polymer may take place at a temperature from about 10° C. to about 150° C., and in other embodiments from about 20° C. to about 100° C. The time required for completing the reaction between the imide compound and the reactive polymer depends on various factors such as the type and amount of the catalyst or initiator used to prepare the reactive polymer, the type and amount of the imide compound, as well as the temperature at which the functionalization reaction is conducted. In one or more embodiments, the reaction between the imide compound and the reactive polymer can be conducted for about 10 to 60 minutes.

In one or more embodiments, after the reaction between the reactive polymer and the imide compound (and optionally the co-functionalizing agent) has been accomplished or completed, a quenching agent can be added to the polymerization mixture in order to inactivate any residual reactive polymer chains and the catalyst or catalyst components. The quenching agent may include a protic compound, which includes, but is not limited to, an alcohol, a carboxylic acid, an inorganic acid, water, or a mixture thereof. An antioxidant such as 2,6-di-tert-butyl-4-methylphenol may be added along with, before, or after the addition of the quenching agent. The amount of the antioxidant employed may be in the range of 0.2% to 1% by weight of the polymer product.

When the polymerization mixture has been quenched, the polymer product can be recovered from the polymerization mixture by using any conventional procedures of desolventization and drying that are known in the art. For instance, the polymer can be recovered by subjecting the polymer cement to steam desolventization, followed by drying the resulting polymer crumbs in a hot air tunnel. Alternatively, the polymer may be recovered by directly drying the polymer cement on a drum dryer. The content of the volatile substances in the dried polymer can be below 1%, and in other embodiments below 0.5% by weight of the polymer.

While the reactive polymer and the imide compound (and optionally the co-functionalizing agent) are believed to react to produce a novel functionalized polymer, the exact chemical structure of the functionalized polymer produced in every embodiment is not known with any great degree of certainty, particularly as the structure relates to the residue imparted to the polymer chain end by the imide compound and optionally the co-functionalizing agent. Indeed, it is speculated that the structure of the functionalized polymer may depend upon various factors such as the conditions employed to prepare the reactive polymer (e.g., the type and amount of the catalyst or initiator) and the conditions employed to react the imide compound (and optionally the co-functionalizing agent) with the reactive polymer (e.g., the types and amounts of the imide compound and the co-functionalizing agent).

In one or more embodiments, the functionalized polymers prepared according to this invention may contain unsaturation. In these or other embodiments, the functionalized polymers are vulcanizable. In one or more embodiments, the functionalized polymers can have a glass transition temperature ($T_g$) that is less than 0° C., in other embodiments less than −20° C., and in other embodiments less than −30° C. In one embodiment, these polymers may exhibit a single glass transition temperature. In particular embodiments, the polymers may be hydrogenated or partially hydrogenated.

In one or more embodiments, the functionalized polymers of this invention may be cis-1,4-polydienes having a cis-1,4-linkage content that is greater than 60%, in other embodiments greater than about 75%, in other embodiments greater than about 90%, and in other embodiments greater than about 95%, where the percentages are based upon the number of diene mer units adopting the cis-1,4 linkage versus the total number of diene mer units. Also, these polymers may have a 1,2-linkage content that is less than about 7%, in other embodiments less than 5%, in other embodiments less than 2%, and in other embodiments less than 1%, where the percentages are based upon the number of diene mer units adopting the 1,2-linkage versus the total number of diene mer units. The balance of the diene mer units may adopt the trans-1,4-linkage. The cis-1,4-, 1,2-, and trans-1,4-linkage contents can be determined by infrared spectroscopy. The number average molecular weight ($M_n$) of these polymers may be from about 1,000 to about 1,000,000, in other embodiments from about 5,000 to about 200,000, in other embodiments from about 25,000 to about 150,000, and in other embodiments from about 50,000 to about 120,000, as determined by using gel permeation chromatography (GPC) calibrated with polystyrene standards and Mark-Houwink constants for the polymer in question. The polydispersity ($M_w/M_n$) of these polymers may be from about 1.5 to about 5.0, and in other embodiments from about 2.0 to about 4.0.

In one or more embodiments, the functionalized polymers of this invention may be polydienes having medium or low cis-1,4-linkage contents. These polymers, which can be prepared by anionic polymerization techniques, can have a cis-1,4-linkage content of from about 10% to 60%, in other embodiments from about 15% to 55%, and in other embodiments from about 20% to about 50%. These polydienes may also have a 1,2-linkage content from about 10% to about 90%, in other embodiments from about 10% to about 60%, in other embodiments from about 15% to about 50%, and in other embodiments from about 20% to about 45%. In particular embodiments, where the polydienes are prepared by employing a functional anionic initiator, the head of the polymer chain includes a functional group that is the residue of the functional initiator.

In particular embodiments, the functionalized polymers of this invention are copolymers of 1,3-butadiene, styrene, and optionally isoprene. These may include random copolymers and block copolymers.

In one or more embodiments, the functionalized polymer is an anionically-polymerized polymer selected from the group consisting of functionalized polybutadiene, functionalized polyisoprene, functionalized poly(styrene-co-butadiene), functionalized poly(styrene-co-butadiene-co-isoprene), functionalized poly(isoprene-co-styrene), and functionalized poly(butadiene-co-isoprene). The number average molecular weight ($M_n$) of these polymers may be from about 1,000 to about 1,000,000, in other embodiments from about 5,000 to about 1,000,000, in other embodiments from about 50,000 to about 500,000, and in other embodiments from about 100,000 to about 300,000, as determined by using gel permeation chromatography (GPC) calibrated with polystyrene standards and Mark-Houwink constants for the polymer in question. The polydispersity ($M_w/M_n$) of these polymers may be from about 1.0 to about 3.0, and in other embodiments from about 1.1 to about 2.0.

Advantageously, the functionalized polymers of this invention exhibit improved cold-flow resistance and provide vulcanizates that demonstrate reduced hysteresis. The functionalized polymers are particularly useful in preparing tire components. These tire components can be prepared by using the functionalized polymers alone or together with other rubbery polymers (i.e., polymers that can be vulcanized to form compositions possessing elastomeric properties). Other rubbery polymers that may be used include natural and synthetic elastomers. The synthetic elastomers typically derive from the polymerization of conjugated diene monomers. These conjugated diene monomers may be copolymerized with other monomers such as vinyl-substituted aromatic monomers. Other rubbery polymers may derive from the polymerization of ethylene together with one or more α-olefins and optionally one or more diene monomers.

Useful rubbery polymers include natural rubber, synthetic polyisoprene, polybutadiene, polyisobutylene-co-isoprene, neoprene, poly(ethylene-co-propylene), poly(styrene-co-butadiene), poly(styrene-co-isoprene), and poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched and star shaped. Other ingredients that are typically employed in rubber compounding may also be added.

The rubber compositions may include fillers such as inorganic and organic fillers. The organic fillers include carbon black and starch. The inorganic fillers may include silica, aluminum hydroxide, magnesium hydroxide, clays (hydrated aluminum silicates), and mixtures thereof.

A multitude of rubber curing agents (also called vulcanizing agents) may be employed, including sulfur or peroxide-based curing systems. Curing agents are described in Kirk-Othmer, ENCYCLOPEDIA OF CHEMICAL TECHNOLOGY, Vol. 20, pgs. 365-468, ($3^{rd}$ Ed. 1982), particularly *Vulcanization Agents and Auxiliary Materials*, pgs. 390-402, and A. Y. Coran, *Vulcanization*, ENCYCLOPEDIA OF POLYMER SCIENCE AND ENGINEERING, ($2^{nd}$ Ed. 1989), which are incorporated herein by reference. Vulcanizing agents may be used alone or in combination.

Other ingredients that may be employed include accelerators, oils, waxes, scorch inhibiting agents, processing aids, zinc oxide, tackifying resins, reinforcing resins, fatty acids such as stearic acid, peptizers, and one or more additional rubbers.

These rubber compositions are useful for forming tire components such as treads, subtreads, black sidewalls, body ply skins, bead filler, and the like. Preferably, the functional polymers are employed in tread and sidewall formulations. In one or more embodiments, these tread formulations may include from about 10% to about 100% by weight, in other embodiments from about 35% to about 90% by weight, and in other embodiments from about 50% to 80% by weight of the functionalized polymer based on the total weight of the rubber within the formulation.

In one or more embodiments, the vulcanizable rubber composition may be prepared by forming an initial masterbatch that includes the rubber component and filler (the rubber component optionally including the functionalized polymer of this invention). This initial masterbatch may be mixed at a starting temperature of from about 25° C. to about 125° C. with a discharge temperature of about 135° C. to about 180° C. To prevent premature vulcanization (also known as scorch), this initial masterbatch may exclude vulcanizing agents. Once the initial masterbatch is processed, the vulcanizing agents may be introduced and blended into the initial masterbatch at low temperatures in a final mixing stage, which preferably does not initiate the vulcanization process. Optionally, additional mixing stages, sometimes called remills, can be employed between the masterbatch mixing stage and the final mixing stage. Various ingredients including the functionalized polymer of this invention can be added during these remills. Rubber compounding techniques and the additives employed therein are generally known as disclosed in *The Compounding and Vulcanization of Rubber*, in *Rubber Technology* (2$^{nd}$ Ed. 1973).

The mixing conditions and procedures applicable to silica-filled tire formulations are also well known as described in U.S. Pat. Nos. 5,227,425, 5,719,207, 5,717,022, and European Patent No. 890,606, all of which are incorporated herein by reference. In one or more embodiments, where silica is employed as a filler (alone or in combination with other fillers), a coupling and/or shielding agent may be added to the rubber formulation during mixing. Useful coupling and shielding agents are disclosed in U.S. Pat. Nos. 3,842,111, 3,873,489, 3,978,103, 3,997,581, 4,002,594, 5,580,919, 5,583,245, 5,663,396, 5,674,932, 5,684,171, 5,684,172 5,696,197, 6,608,145, 6,667,362, 6,579,949, 6,590,017, 6,525,118, 6,342,552, and 6,683,135, which are incorporated herein by reference. In one embodiment, the initial masterbatch is prepared by including the functionalized polymer of this invention and silica in the substantial absence of coupling and shielding agents.

Where the vulcanizable rubber compositions are employed in the manufacture of tires, these compositions can be processed into tire components according to ordinary tire manufacturing techniques including standard rubber shaping, molding and curing techniques. Typically, vulcanization is effected by heating the vulcanizable composition in a mold; e.g., it may be heated to about 140 to about 180° C. Cured or crosslinked rubber compositions may be referred to as vulcanizates, which generally contain three-dimensional polymeric networks that are thermoset. The other ingredients, such as processing aides and fillers, may be evenly dispersed throughout the vulcanized network. Pneumatic tires can be made as discussed in U.S. Pat. Nos. 5,866,171, 5,876,527, 5,931,211, and 5,971,046, which are incorporated herein by reference.

In order to demonstrate the practice of the present invention, the following examples have been prepared and tested. The examples should not, however, be viewed as limiting the scope of the invention. The claims will serve to define the invention.

EXAMPLES

Example 1

Synthesis of
N-[3-Bis(trimethylsilyl)amino-1-propyl]phthalimide
(BTMSAPPI)

About 4.60 g of potassium phthalimide, 6.37 g of N,N-bis(trimethylsilyl)-3-bromo-1-propylamine, and 15 mL of N,N-dimethylformamide were mixed in a flask. The mixture was stirred for 6 hour while the flask was kept in an oil bath maintained at 80° C. The N,N-dimethylformamide was removed under vacuum. The residue was extracted with 90 mL of cyclohexane and filtered. The filtrate was evaporated under vacuum. The residue was triturated with 80 mL of hexane, cooled with dry ice, and then filtered to give N-[3-bis(trimethylsilyl)amino-1-propyl]phthalimide (BTMSAPPI) as a white solid (5.95 g, 76% yield). $^1$H NMR data ($C_6D_6$, 25° C., referenced to tetramethylsilane) of the product: δ 7.41 (multiplet, 2H, aromatic protons), 6.85 (multiplet, 2H, aromatic protons), 3.44 (triplet, J=7.1 Hz, 2H, $CH_2$ protons), 2.81 (multiplet, 2H, $CH_2$ protons), 1.75 (multiplet, 2H, $CH_2$ protons), 0.06 (singlet, 18H, Si—$CH_3$ protons).

Example 2

Synthesis of N-[3-(2,2,5,5-Tetramethyl-1-aza-2,5-disila-1-cyclopentyl)-1-propyl]phthalimide (TMADSCPPI)

About 3.36 g of potassium phthalimide, 4.89 g of 1-(3-bromopropyl)-2,2,5,5-tetramethyl-1-aza-2,5-disilacyclopentane, and 12 mL of N,N-dimethylformamide were mixed in a flask. The mixture was stirred for 5 hour while the flask was kept in an oil bath maintained at 75° C. The N,N-dimethylformamide was removed under vacuum. The residue was extracted with 90 mL of toluene and filtered. The filtrate was evaporated under vacuum. The residue was triturated with 80 mL of hexane, cooled with dry ice, and then filtered to give N-[3-(2,2,5,5-tetramethyl-1-aza-2,5-disila-1-cyclopentyl)-1-propyl]phthalimide (TMADSCPPI) as a white solid (4.3 g, 68% yield). $^1$H NMR data ($C_6D_6$, 25° C., referenced to tetramethylsilane) of the product: δ 7.41 (multiplet, 2H, aromatic protons), 6.81 (multiplet, 2H, aromatic protons), 3.55 (multiplet, 2H, $CH_2$ protons), 2.79 (multiplet, 2H, $CH_2$ protons), 1.77 (multiplet, 2 H, $CH_2$ protons), 0.70 (singlet, 4H, $CH_2$—Si protons), 0.06 (singlet, 12H, Si—$CH_3$ protons).

Example 3

Synthesis of Unmodified cis-1,4-Polybutadiene

To a 2-gallon nitrogen-purged reactor equipped with turbine agitator blades were added 1383 g of hexane and 3083 g of 20.6 wt % butadiene in hexane. A preformed catalyst was prepared by mixing 8.08 ml of 4.32 M methylaluminoxane in toluene, 1.83 g of 20.6 wt % 1,3-butadiene in hexane, 0.65 ml of 0.537 M neodymium versatate in cyclohexane, 7.33 ml of 1.0 M diisobutylaluminum hydride in hexane, and 1.40 ml of 1.0 M diethylaluminum chloride in hexane. The catalyst was aged for 15 minutes and charged into the reactor. The reactor jacket temperature was then set to 65° C. Forty five minutes after addition of the catalyst, the polymerization mixture was cooled to room temperature. The resulting polymer cement was coagulated with 12 liters of isopropanol containing 5 g of 2,6-di-tert-butyl-4-methylphenol and then drum-dried. The Mooney viscosity ($ML_{1+4}$) of the resulting polymer was determined to be 26.5 at 100° C. by using a Monsanto Mooney viscometer with a large rotor, a one-minute warm-up time, and a four-minute running time. As determined by gel permeation chromatography (GPC), the polymer had a number average molecular weight ($M_n$) of 111,800, a weight average molecular weight ($M_w$) of 209,500, and a molecular weight distribution ($M_w/M_n$) of 1.87. The infrared spectroscopic analysis of the polymer indicated a cis-1,4-linkage content of 94.4%, a trans-1,4-linkage content of 5.1%, and a 1,2-linkage content of 0.5%.

The cold-flow resistance of the polymer was measured by using a Scott plasticity tester. Approximately 2.6 g of the polymer was molded, at 100° C. for 20 minutes, into a cylindrical button with a diameter of 15 mm and a height of 12 mm. After cooling down to room temperature, the button was removed from the mold and placed in a Scott plasticity tester at room temperature. A 5-kg load was applied to the specimen. After 8 minutes, the residual gauge (i.e., sample thickness) was measured and taken as an indication of the cold-flow resistance of the polymer. Generally, a higher residual gauge value indicates better cold-flow resistance.

The properties of the unmodified cis-1,4-polybutadiene are summarized in Table 1.

TABLE 1

Physical Properties of Unmodified and Modified cis-1,4-Polybutadiene

| | Example No. | | | | |
|---|---|---|---|---|---|
| | Example 3 | Example 4 | Example 5 | Example 6 | Example 7 (Comparative) |
| Polymer type | unmodified | unmodified | BTMSAPPI-modified | TMADSCPPI-modified | EPI-modified |
| $ML_{1+4}$ at 100° C. | 26.5 | 44.2 | 38.2 | 42.9 | 22.4 |
| $M_n$ | 111,800 | 130,700 | 75.8 | 74.2 | 93,700 |
| $M_w$ | 209,500 | 260,500 | 188.7 | 188.0 | 195,300 |
| $M_w/M_n$ | 1.87 | 1.99 | 2.49 | 2.53 | 2.09 |
| Cold-flow gauge (mm at 8 min.) | 1.72 | 2.28 | 2.80 | 2.86 | 1.52 |
| % cis-1,4 | 94.4 | 95.0 | 94.2 | 94.2 | 94.1 |
| % trans-1,4 | 5.1 | 4.5 | 5.3 | 5.3 | 5.4 |
| % 1, 2 | 0.5 | 0.5 | 0.5 | 0.5 | 0.5 |

Example 4

Synthesis of Unmodified cis-1,4-Polybutadiene

To a 2-gallon nitrogen-purged reactor equipped with turbine agitator blades were added 1631 g of hexane and 2835 g of 22.4 wt % butadiene in hexane. A preformed catalyst was prepared by mixing 6.10 ml of 4.32 M methylaluminoxane in toluene, 1.27 g of 22.4 wt % 1,3-butadiene in hexane, 0.49 ml of 0.537 M neodymium versatate in cyclohexane, 5.53 ml of 1.0 M diisobutylaluminum hydride in hexane, and 1.05 ml of 1.0 M diethylaluminum chloride in hexane. The catalyst was aged for 15 minutes and charged into the reactor. The reactor jacket temperature was then set to 65° C. Seventy two minutes after addition of the catalyst, the polymerization mixture was cooled to room temperature. The resulting polymer cement was coagulated with 12 liters of isopropanol containing 5 g of 2,6-di-tert-butyl-4-methylphenol and then drum-dried. The properties of the resulting polymer are summarized in Table 1.

Example 5

Synthesis of cis-1,4-Polybutadiene Modified with N-[3-Bis(trimethylsilyl)amino-1-propyl]phthalimide (BTMSAPPI)

To a 2-gallon nitrogen-purged reactor equipped with turbine agitator blades were added 1526 g of hexane and 2940 g of 21.6 wt % butadiene in hexane. A preformed catalyst was prepared by mixing 9.55 ml of 4.32 M methylaluminoxane in toluene, 2.06 g of 21.6 wt % 1,3-butadiene in hexane, 0.77 ml of 0.537 M neodymium versatate in cyclohexane, 8.67 ml of 1.0 M diisobutylaluminum hydride in hexane, and 1.65 ml of 1.0 M diethylaluminum chloride in hexane. The catalyst was aged for 15 minutes and charged into the reactor. The reactor jacket temperature was then set to 65° C. Fifty minutes after addition of the catalyst, the polymerization mixture was cooled to room temperature.

About 424 g of the resulting unmodified polymer cement was transferred from the reactor to a nitrogen-purged bottle, followed by addition of 14.0 ml of 0.220 M N-[3-bis(trimethylsilyl)amino-1-propyl]phthalimide (BTMSAPPI) in toluene. The bottle was tumbled for 25 minutes in a water bath maintained at 65° C. The resulting mixture was coagulated with 3 liters of isopropanol containing 0.5 g of 2,6-di-tert-butyl-4-methylphenol and then drum-dried. The properties of the resulting BTMSAPPI-modified polymer are summarized in Table 1.

Example 6

Synthesis of cis-1,4-Polybutadiene Modified with N-[3-(2,2,5,5-tetramethyl-1-aza-2,5-disila-1-cyclopentyl)-1-propyl]phthalimide (TMADSCPPI)

About 419 g of the living polymer cement as synthesized in Example 5 was transferred from the reactor to a nitrogen-purged bottle, followed by addition of 18.9 ml of 0.161 M N-[3-(2,2,5,5-tetramethyl-1-aza-2,5-disila-1-cyclopentyl)-1-propyl]phthalimide (TMADSCP) in toluene. The bottle was tumbled for 25 minutes in a water bath maintained at 65° C. The resulting mixture was coagulated with 3 liters of isopropanol containing 0.5 g of 2,6-di-tert-butyl-4-methylphenol and then drum-dried. The properties of the resulting TMADSCPPI-modified polymer are summarized in Table 1.

Example 7 (Comparative Example)

Synthesis of cis-1,4-Polybutadiene Modified with N-Ethylphthalimide (EPI)

About 430 g of the living polymer cement as synthesized in Example 4 was transferred from the reactor to a nitrogen-purged bottle, followed by addition of 11.1 ml of 0.282 M N-ethylphthalimide (EPI) in toluene. The bottle was tumbled for 25 minutes in a water bath maintained at 65° C. The resulting mixture was coagulated with 3 liters of isopropanol containing 0.5 g of 2,6-di-tert-butyl-4-methylphenol and then drum-dried. The properties of the resulting EPI-modified polymer are summarized in Table 1.

In FIG. 1, the cold-flow resistance of the unmodified and modified cis-1,4-polybutadiene samples synthesized in Examples 3-7 is plotted against the polymer Mooney viscosity. The data indicate that, at the same polymer Mooney viscosity, the BTMSAPPI- and TMADSCPPI-modified cis-1,4-polybutadiene samples show higher residual cold-flow gauge values and accordingly better cold-flow resistance than the unmodified polymer. In contrast, the EPI-modified cis-1,4-polybutadiene sample provides no improvement in cold-flow resistance as compared to the unmodified polymer.

The Mooney viscosity ($ML_{1+4}$) of the uncured compound was determined at 130° C. by using a Alpha Technologies Mooney viscometer with a large rotor, a one-minute warm-up time, and a four-minute running time. The tensile strength at break ($T_b$) and the elongation at break ($E_b$) were determined according to ASTM D412. The Payne effect data ($\Delta G'$) and hysteresis data (tan $\delta$) of the vulcanizates were obtained from a dynamic strain sweep experiment, which was conducted at 50° C. and 15 Hz with strain sweeping from 0.1% to 20%. $\Delta G'$ is the difference between G' at 0.1% strain and G' at 20% strain. The physical properties of the vulcanizates are summarized in Table 3 and FIG. 2.

TABLE 3

Physical Properties of Rubber Vulcanizates Prepared from cis-1,4-Polybutadiene

| | Example No. | | | | |
|---|---|---|---|---|---|
| | Example 8 | Example 9 | Example 10 | Example 11 | Example 12 (Comparative) |
| Polymer used | Example 3 | Example 4 | Example 5 | Example 6 | Example 7 |
| Polymer type | unmodified | unmodified | BTMSAPPI-modified | TMADSCPPI-modified | EPI-modified |
| Compound $ML_{1+4}$ at 130° C. | 50.9 | 66.7 | 66.0 | 64.5 | 44.2 |
| $T_b$ at 23° C. (MPa) | 14.9 | 17.4 | 17.0 | 16.3 | 14.5 |
| $E_b$ at 23° C. (%) | 423 | 424 | 412 | 395 | 394 |
| $\Delta G'$ (MPa) | 2.79 | 2.34 | 1.21 | 1.47 | 2.56 |
| tan$\delta$ at 50° C., 3% strain | 0.137 | 0.119 | 0.0951 | 0.0952 | 0.156 |

Examples 8-12

Compounding Evaluation of BTMSAPPI-, TMADSCPPI-, and EPI-modified cis-1,4-Polybutadiene vs. Unmodified cis-1,4-Polybutadiene The unmodified and modified cis-1,4-polybutadiene samples produced in Examples 3-7 were evaluated in a rubber compound filled with carbon black. The compositions of the vulcanizates are presented in Table 2, wherein the numbers are expressed as parts by weight per hundred parts by weight of rubber (phr).

TABLE 2

Compositions of Rubber Vulcanizates Prepared from cis-1,4-Polybutadiene

| Ingredient | Amount (phr) |
|---|---|
| Cis-1,4-Polybutadiene | 80 |
| Polyisoprene | 20 |
| Carbon black | 50 |
| Oil | 10 |
| Wax | 2 |
| Antioxidant | 1 |
| Zinc oxide | 2.5 |
| Stearic acid | 2 |
| Accelerators | 1.3 |
| Sulfur | 1.5 |
| Total | 170.3 |

Figure 2:
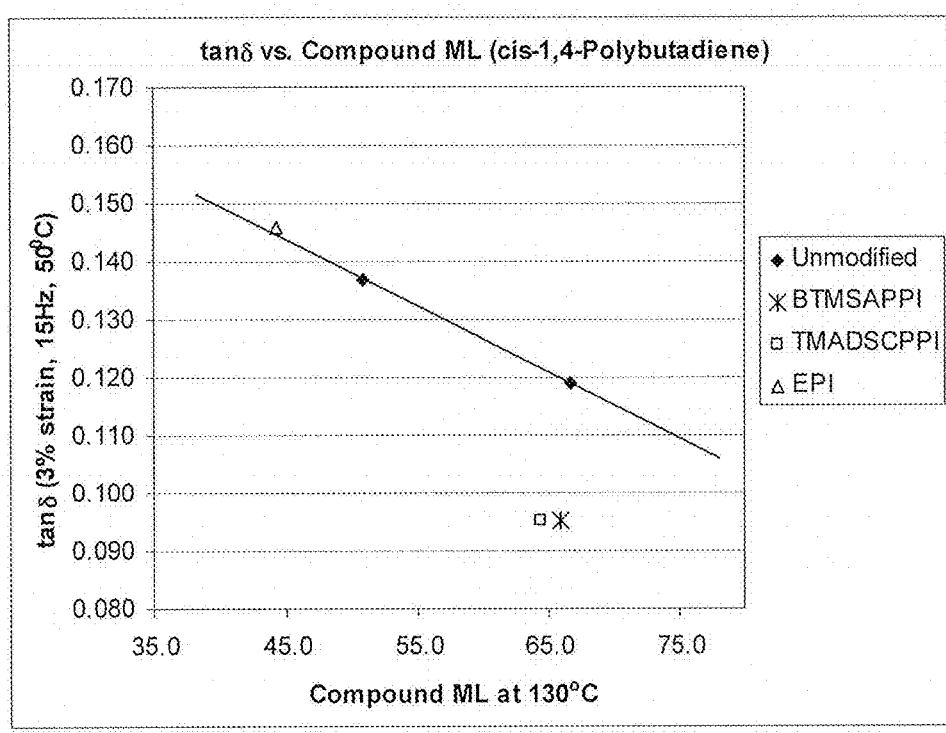
FIG. 2 is a graphical plot of hysteresis loss (tan δ) versus Mooney viscosity (ML 1+4 at 130° C.) for vulcanizates prepared from functionalized cis-1,4-polybutadiene prepared according to one or more embodiments of the present invention as compared to vulcanizates prepared from unfunctionalized cis-1,4-polybutadiene.

As can be seen in Table 3 and FIG. 2, the BTMSAPPI- and TMADSCPPI-modified cis-1,4-polybutadiene samples give lower tan $\delta$ at 50° C. than the unmodified polymer, indicating that the modification of cis-1,4-polybutadiene with BTMSAPPI and TMADSCPPI reduces hysteresis. The BTMSAPPI- and TMADSCPPI-modified cis-1,4-polybutadiene samples also give lower $\Delta G'$ than the unmodified polymer, indicating that the Payne Effect has been reduced due to the stronger interaction between the modified polymer and carbon black. In contrast, the EPI-modified cis-1,4-polybutadiene sample provides no significant reduction in hysteresis and the Payne effect as compared to the unmodified polymer.

Example 13

Synthesis of Unmodified Poly(Styrene-Co-Butadiene)

To a 5-gallon nitrogen-purged reactor equipped with turbine agitator blades were added 5031 g of hexane, 1320 g of 33.0 wt % styrene in hexane, and 8064 g of 21.6 wt % 1,3-butadiene in hexane. To the reactor were charged 11.34 ml of 1.6 M n-butyllithium in hexane and 3.74 ml of 1.6 M 2,2-di(tetrahydrofuryl)propane in hexane. The batch was heated by applying hot water to the reactor jacket. Once the batch temperature reached 50° C., the reactor jacket was cooled with cold water. Ninety minutes after the addition of the catalyst, about 410 g of the resulting living polymer cement was transferred from the reactor into a nitrogen-purged bottle and quenched by addition of 3 ml of isopropanol containing 0.3 g of 2,6-di-tert-butyl-4-methylphenol. The resulting mixture was coagulated with 3 liters of isopropanol containing 0.5 g of 2,6-di-tert-butyl-4-methylphenol and then drum-dried. The $^1$H NMR analysis of the polymer indicated that the polymer had a styrene content of 20.6 wt % and a 1,2-linkage content (butadiene unit) of 57.4%. As measured by differential scanning calorimetry (DSC), the polymer had a glass transition temperature (Tg) of −32° C.

The cold-flow resistance of the unmodified poly(styrene-co-butadiene) was measured by using a Scott plasticity tester. The procedure is similar to that described in Example 3, except that the residual gauge (i.e., sample thickness) was measured at 30 minutes after a 5-kg load was applied to the sample.

The properties of the resulting unmodified poly(styrene-co-butadiene) are summarized in Table 4.

TABLE 4

Physical Properties of Unmodified and Modified Poly(styrene-co-butadiene)

| | Example No. | | | |
|---|---|---|---|---|
| | Example 13 | Example 14 | Example 15 | Example 16 |
| Polymer type | unmodified | unmodified | BTMSAPPI-modified | TMADSCPPI-modified |
| $ML_{1+4}$ at 100° C. | 11.5 | 49.5 | 14.6 | 17.0 |
| $M_n$ | 120,300 | 185,500 | 123,900 | 126,900 |
| $M_w$ | 125,200 | 194,800 | 132,700 | 140,200 |
| $M_w/M_n$ | 1.04 | 1.05 | 1.07 | 1.10 |
| Cold-flow gauge (mm at 30 min.) | 2.21 | 3.11 | 2.52 | 2.68 |
| % styrene | 20.6 | 20.0 | 20.6 | 20.6 |
| % 1, 2 | 57.4 | 55.5 | 57.4 | 57.4 |
| $T_g$ (° C.) | −32 | −31 | −32 | −32 |

Example 14

Synthesis of Unmodified Poly(Styrene-Co-Butadiene)

To a 2-gallon nitrogen-purged reactor equipped with turbine agitator blades was added 1597 g of hexane, 399 g of 34.0 wt % styrene in hexane, and 2440 g of 22.3 wt % 1,3-butadiene in hexane. To the reactor was charged 2.58 mL of 1.6 M n-butyllithium in hexane and 0.85 mL of 1.6 M 2,2-bis(2'-tetrahydrofuryl)propane in hexane. The batch was heated by applying hot water to the reactor jacket. Once the batch temperature reached 55° C., the reactor jacket was cooled with cold water. Two hours after the addition of the catalyst, the polymer cement was removed from the reactor and coagulated with 3 gallons of isopropanol containing 7 g of 2,6-di-tert-butyl-4-methylphenol, and then drum-dried. The properties of the resulting unmodified SBR are summarized in Table 4.

Example 15

Synthesis of Poly(styrene-co-butadiene) Modified with N-[3-Bis(trimethylsilyl)amino-1-propyl]phthalimide (BTMSAPPI)

About 414 g of the living polymer cement as synthesized in Example 13 was transferred from the reactor to a nitrogen-purged bottle, followed by addition of 2.35 ml of 0.220 M N-[3-bis(trimethylsilyl)amino-1-propyl]phthalimide (BTMSAPPI) in toluene. The bottle was tumbled for 15 minutes in a water bath maintained at 65° C. The resulting mixture was coagulated with 3 liters of isopropanol containing 0.5 g of 2,6-di-tert-butyl-4-methylphenol and then drum-dried. The properties of the resulting BTMSAPPI-modified polymer are summarized in Table 4.

Example 16

Synthesis of Poly(styrene-co-butadiene) Modified with N-[3-(2,2,5,5-tetramethyl-1-aza-2,5-disila-1-cyclopentyl)-1-propyl]phthalimide (TMADSCPPI)

About 408 g of the living polymer cement as synthesized in Example 13 was transferred from the reactor to a nitrogen-purged bottle, followed by addition of 3.17 ml of 0.161 M N-[3-(2,2,5,5-tetramethyl-1-aza-2,5-disila-1-cyclopentyl)-1-propyl]phthalimide (TMADSCPPI) in toluene. The bottle was tumbled for 15 minutes in a water bath maintained at 65° C. The resulting mixture was coagulated with 3 liters of isopropanol containing 0.5 g of 2,6-di-tert-butyl-4-methylphenol and then drum-dried. The properties of the resulting TMADSCPPI-modified polymer are summarized in Table 4.

In FIG. 3, the cold-flow resistance of the unmodified and modified poly(styrene-co-butadiene) samples synthesized in Examples 13-16 is plotted against the polymer Mooney viscosity. The data indicate that, at the same polymer Mooney viscosity, the BTMSAPPI- and TMADSCPPI-modified poly(styrene-co-butadiene) samples show higher residual cold-flow gauge values and accordingly better cold-flow resistance than the unmodified polymer.

Examples 17-20

Compounding Evaluation of BTMSAPPI- and TMADSCPPI-Modified Poly(styrene-co-butadiene) Versus Unmodified Poly(styrene-co-butadiene)

The unmodified and modified poly(styrene-co-butadiene) samples produced in Examples 13-16 were evaluated in a rubber compound filled with carbon black. The compositions of the vulcanizates are presented in Table 5, wherein the numbers are expressed as parts by weight per hundred parts by weight of rubber (phr).

TABLE 5

Compositions of Rubber Vulcanizates Prepared from Poly(styrene-co-butadiene)

| Ingredient | Amount (phr) |
|---|---|
| SBR | 100 |
| Carbon black | 50 |
| Oil | 10 |
| Wax | 2 |
| Antioxidant | 0.95 |
| Zinc oxide | 2.5 |
| Stearic acid | 2 |
| Accelerators | 1.3 |
| Sulfur | 1.5 |
| Total | 170.25 |

The Mooney viscosity ($ML_{1+4}$) of the uncured compound was determined at 100° C. by using a Alpha Technologies Mooney viscometer with a large rotor, a one-minute warm-up time, and a four-minute running time. The tensile strength at break ($T_b$) and the elongation at break ($E_b$) were determined according to ASTM D412. The Payne effect data (ΔG') and hysteresis data (tan δ) of the vulcanizates were obtained from a dynamic strain sweep experiment, which was conducted at 60° C. and 10 Hz with strain sweeping from 0.25% to 15%.

ΔG' is the difference between G' at 0.25% strain and G' at 14% strain. The physical properties of the vulcanizates are summarized in Table 6 and FIG. 4.

TABLE 6

Physical Properties of Rubber Vulcanizates Prepared from Poly(styrene-co-butadiene)

| | Example No. | | | |
|---|---|---|---|---|
| | Example 17 | Example 18 | Example 19 | Example 20 |
| Polymer used | Example 13 | Example 14 | Example 15 | Example 16 |
| Polymer type | unmodified | unmodified | BTMSAPPI-modified | TMADSCPPI-modified |
| Compound ML at 100° C. | 36.3 | 89.1 | 74.6 | 75.0 |
| $T_b$ at 23° C. (MPa) | 15.0 | 17.6 | 21.5 | 20.0 |
| $E_b$ at 23° C. (%) | 362 | 529 | 359 | 344 |
| ΔG' (MPa) | 4.01 | 1.78 | 0.38 | 0.46 |
| tan δ at 60° C., 5% strain | 0.245 | 0.157 | 0.103 | 0.112 |

As can be seen in Table 6 and FIG. 4, the BTMSAPPI- and TMADSCPPI-modified poly(styrene-co-butadiene) samples give lower tan δ at 60° C. than the unmodified polymer, indicating that the modification of poly(styrene-co-butadiene) with BTMSAPPI and TMADSCPPI reduces hysteresis. The BTMSAPPI- and TMADSCPPI-modified poly(styrene-co-butadiene) samples also give lower ΔG' than the unmodified polymer, indicating that the Payne Effect has been reduced due to the interaction between the modified polymer and carbon black.

Various modifications and alterations that do not depart from the scope and spirit of this invention will become apparent to those skilled in the art. This invention is not to be duly limited to the illustrative embodiments set forth herein.

What is claimed is:

1. A method for preparing a functionalized polymer, the method comprising the steps of:
   (i) preparing a living or pseudo-living polymer having a reactive chain end and
   (ii) reacting the reactive chain end with an imide compound defined by one or more of the formulae:

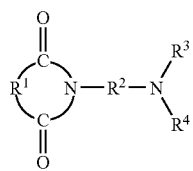

where $R^1$ and $R^2$ are each independently a divalent organic group, and $R^3$ and $R^4$ are each independently a mono-valent organic group or a hydrolyzable group, or R.sup.3 and R.sup.4 join to form a divalent organic group,

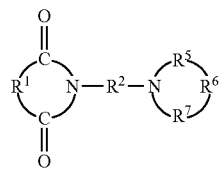

where $R^1$ and $R^2$, and $R^6$ are each independently a divalent organic group, and $R^5$ and $R^7$ are each independently a bond or a hydrolyzable group,

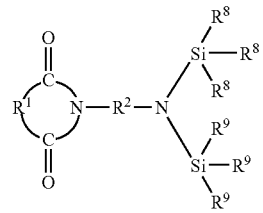

where $R^1$ and $R^2$ are each independently a divalent organic group, and $R^8$ and $R^9$ are each independently a hydrogen atom or a mono-valent organic group, or at least one $R^8$ and at least one $R^9$ join to form a divalent organic group, and

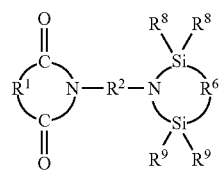

where $R^1$ and $R^2$, and $R^6$ are each independently a divalent organic group, and $R^8$ and $R^9$ are each independently a hydrogen atom or a mono-valent organic group.

2. The method of claim 1, where at least one of $R^3$ and $R^4$ is a hydrolyzable group.

3. The method of claim 2, where the hydrolyzable group is selected from the group consisting of trihydrocarbylsilyl and dihydrocarbylhydrosilyl groups.

4. The method of claim 1, where the imide compound is selected from the group consisting of N-[bis(trihydrocarbylsilyl)aminohydrocarbyl]imide, N-[bis(dihydrocarbylhydrosilyl)aminohydrocarbyl]imide, N-[(1-aza-disila-1-cyclohydrocarbyl)hydrocarbyl]imide, N-[(trihydrocarbylsilyl)(hydrocarbyl)aminohydrocarbyl]imide, N-[(dihydrocarbylhydrosilyl)(hydrocarbyl)aminohydrocarbyl]imide, N-[(1-aza-2-sila-1-cyclohydrocarbyl)hydrocarbyl]imide, N-(dihydrocarbylaminohydrocarbyl)imide, and N-[(1-aza-1-cyclohydrocarbyl)hydrocarbyl]imide compounds.

5. The method of claim 4, where the imide compound is a N-[bis(trihydrocarbylsilyl)aminohydrocarbyl]imide compound selected from the group consisting of N-[3-bis(trimethylsilyl)amino-1-propyl]phthalimide, N-[3-bis(triethylsilyl)amino-1-propyl]phthalimide, N-[3-bis(triphenylsilyl)amino-1-propyl]phthalimide, N-[2-bis(trimethylsilyl)amino-1-propyl]phthalimide, N-[2-bis(triethylsilyl)amino-1-propyl]phthalimide, N-[2-bis(triphenylsilyl)amino-1-propyl]phthalimide, N-[4-bis(trimethylsilyl)amino-1-butyl]phthalimide, N-[4-bis(triethylsilyl)amino-1-butyl]phthalimide, N-[4-bis(triphenylsilyl)amino-1-butyl]

phthalimide, N-[3-bis(trimethylsilyl)amino-1-propyl]maleimide, N-[3-bis(triethylsilyl)amino-1-propyl]maleimide, N-[3-bis(triphenylsilyl)amino-1-propyl]maleimide, N-[3-bis(trimethylsilyl)amino-1-propyl]citraconimide, N-[3-bis(triethylsilyl)amino-1-propyl]citraconimide, N-[3-bis(triphenylsilyl)amino-1-propyl]citraconimide, N-[3-bis(trimethylsilyl)amino-1-propyl]succinimide, N-[3-bis(triethylsilyl)amino-1-propyl]succinimide, N-[3-bis(triphenylsilyl)amino-1-propyl]succinimide, N-[3-bis(trimethylsilyl)amino-1-propyl]-1,8-naphthalimide, N-[3-bis(triethylsilyl)amino-1-propyl]-1,8-naphthalimide, N-[3-bis(triphenylsilyl)amino-1-propyl]-1,8-naphthalimide, N-[3-bis(trimethylsilyl)amino-1-propyl]-2,3-naphthalimide, N-[3-bis(triethylsilyl)amino-1-propyl]-2,3-naphthalimide, N-[3-bis(triphenylsilyl)amino-1-propyl]-2,3-naphthalimide, N-[3-bis(trimethylsilyl)amino-1-propyl]-1,2-cyclopentanedicarboximide, N-[3-bis(triethylsilyl)amino-1-propyl]-1,2-cyclopentanedicarboximide, N-[3-bis(triphenylsilyl)amino-1-propyl]-1,2-cyclopentanedicarboximide, N-[3-bis(trimethylsilyl)amino-1-propyl]-1,2-cyclohexanedicarboximide, N-[3-bis(triethylsilyl)amino-1-propyl]-1,2-cyclohexanedicarboximide, and N-[3-bis(triphenylsilyl)amino-1-propyl]-1,2-cyclohexanedicarboximide.

6. The method of claim 4, where the imide compound is a N-[bis(dihydrocarbylhydrosilyl)aminohydrocarbyl]imide compound selected from the group consisting of N-[3-bis(dimethylhydrosilyl)amino-1-propyl]phthalimide, N-[3-bis(diphenylhydrosilyl)amino-1-propyl]maleimide, N-[3-bis(dimethylhydrosilyl)amino-1-propyl]citraconimide, N-[3-bis(diphenylhydrosilyl)amino-1-propyl]succinimide, N-[3-bis(diethylhydrosilyl)amino-1-propyl]-1,8-naphthalimide, N-[3-bis(diethylhydrosilyl)amino-1-propyl]-2,3-naphthalimide, N-[3-bis(dimethylhydrosilyl)amino-1-propyl]-1,2-cyclopentanedicarboximide, and N-[3-bis(diethylhydrosilyl)amino-1-propyl]-1,2-cyclohexanedicarboximide.

7. The method of claim 4, where the imide compound is a N-[(1-aza-disila-1-cyclohydrocarbyl)hydrocarbyl]imide compound selected from the group consisting of N-[3-(2,2,5,5-tetramethyl-1-aza-2,5-disila-1-cyclopentyl)-1-propyl]phthalimide, N-[3-(2,2,5,5-tetraethyl-1-aza-2,5-disila-1-cyclopentyl)-1-propyl]phthalimide, N-[3-(2,2,5,5-tetraphenyl-1-aza-2,5-disila-1-cyclopentyl)-1-propyl]phthalimide, N-[2-(2,2,5,5-tetramethyl-1-aza-2,5-disila-1-cyclopentyl)-1-propyl]phthalimide, N-[2-(2,2,5,5-tetraethyl-1-aza-2,5-disila-1-cyclopentyl)-1-propyl]phthalimide, N-[2-(2,2,5,5-tetraphenyl-1-aza-2,5-disila-1-cyclopentyl)-1-propyl]phthalimide, N-[4-(2,2,5,5-tetramethyl-1-aza-2,5-disila-1-cyclopentyl)-1-butyl]phthalimide, N-[4-(2,2,5,5-tetraethyl-1-aza-2,5-disila-1-cyclopentyl)-1-butyl]phthalimide, N-[4-(2,2,5,5-tetraphenyl-1-aza-2,5-disila-1-cyclopentyl)-1-butyl]phthalimide, N-[3-(2,2,6,6-tetramethyl-1-aza-2,6-disila-1-cyclohexyl)-1-propyl]phthalimide, N-[3-(2,2,6,6-tetraethyl-1-aza-2,6-disila-1-cyclohexyl)-1-propyl]phthalimide, N-[3-(2,2,6,6-tetraphenyl-1-aza-2,6-disila-1-cyclohexyl)-1-propyl]phthalimide, N-[3-(2,2,5,5-tetramethyl-1-aza-2,5-disila-1-cyclopentyl)-1-propyl]maleimide, N-[3-(2,2,5,5-tetraethyl-1-aza-2,5-disila-1-cyclopentyl)-1-propyl]maleimide, N-[3-(2,2,5,5-tetraphenyl-1-aza-2,5-disila-1-cyclopentyl)-1-propyl]maleimide, N-[3-(2,2,5,5-tetramethyl-1-aza-2,5-disila-1-cyclopentyl)-1-propyl]citraconimide, N-[3-(2,2,5,5-tetraethyl-1-aza-2,5-disila-1-cyclopentyl)-1-propyl]citraconimide, N-[3-(2,2,5,5-tetraphenyl-1-aza-2,5-disila-1-cyclopentyl)-1-propyl]citraconimide, N-[3-(2,2,5,5-tetramethyl-1-aza-2,5-disila-1-cyclopentyl)-1-propyl]succinimide, N-[3-(2,2,5,5-tetraethyl-1-aza-2,5-disila-1-cyclopentyl)-1-propyl]succinimide, N-[3-(2,2,5,5-tetraphenyl-1-aza-2,5-disila-1-cyclopentyl)-1-propyl]succinimide, N-[3-(2,2,5,5-tetramethyl-1-aza-2,5-disila-1-cyclopentyl)-1-propyl]-1,8-naphthalimide, N-[3-(2,2,5,5-tetraethyl-1-aza-2,5-disila-1-cyclopentyl)-1-propyl]-1,8-naphthalimide, N-[3-(2,2,5,5-tetraphenyl-1-aza-2,5-disila-1-cyclopentyl)-1-propyl]-1,8-naphthalimide, N-[3-(2,2,5,5-tetramethyl-1-aza-2,5-disila-1-cyclopentyl)-1-propyl]-2,3-naphthalimide, N-[3-(2,2,5,5-tetraethyl-1-aza-2,5-disila-1-cyclopentyl)-1-propyl]-2,3-naphthalimide, N-[3-(2,2,5,5-tetraphenyl-1-aza-2,5-disila-1-cyclopentyl)-1-propyl]-2,3-naphthalimide, N-[3-(2,2,5,5-tetramethyl-1-aza-2,5-disila-1-cyclopentyl)-1-propyl]-1,2-cyclopentanedicarboximide, N-[3-(2,2,5,5-tetraethyl-1-aza-2,5-disila-1-cyclopentyl)-1-propyl]-1,2-cyclopentanedicarboximide, N-[3-(2,2,5,5-tetraphenyl-1-aza-2,5-disila-1-cyclopentyl)-1-propyl]-1,2-cyclopentanedicarboximide, N-[3-(2,2,5,5-tetramethyl-1-aza-2,5-disila-1-cyclopentyl)-1-propyl]-1,2-cyclohexanedicarboximide, N-[3-(2,2,5,5-tetraethyl-1-aza-2,5-disila-1-cyclopentyl)-1-propyl]-1,2-cyclohexanedicarboximide, and N-[3-(2,2,5,5-tetraphenyl-1-aza-2,5-disila-1-cyclopentyl)-1-propyl]-1,2-cyclohexanedicarboximide.

8. The method of claim 4, where the imide compound is a N-[(trihydrocarbylsilyl)(hydrocarbyl)aminohydrocarbyl]imide compound selected from the group consisting of N-[3-(trimethylsilyl)(methyl)amino-1-propyl]phthalimide, N-[3-(triphenylsilyl)(methyl)amino-1-propyl]maleimide, N-[3-(trimethylsilyl)(methyl)amino-1-propyl]citraconimide, N-[3-(triphenylsilyl)(methyl)amino-1-propyl]succinimide, N-[3-(triethylsilyl)(methyl)amino-1-propyl]-1,8-naphthalimide, N-[3-(triethylsilyl)(methyl)amino-1-propyl]-2,3-naphthalimide, N-[3-(trimethylsilyl)(methyl)amino-1-propyl]-1,2-cyclopentanedicarboximide, and N-[3-(triethylsilyl)(methyl)amino-1-propyl]-1,2-cyclohexanedicarboximide.

9. The method of claim 4, where the imide compound is a N-[(dihydrocarbylhydrosilyl)(hydrocarbyl)aminohydrocarbyl]imide compound selected from the group consisting of N-[3-(dimethylhydrosilyl)(methyl)amino-1-propyl]phthalimide, N-[3-(diphenylhydrosilyl)(methyl)amino-1-propyl]maleimide, N-[3-(dimethylhydrosilyl 1)(methyl)amino-1-propyl]citraconimide, N-[3-(diphenylhydrosilyl)(methyl)amino-1-propyl]succinimide, N-[3-(diethylhydrosilyl)(methyl)amino-1-propyl]-1,8-naphthalimide, N-[3-(diethylhydrosilyl)(methyl)amino-1-propyl]-2,3-naphthalimide, N-[3-(dimethylhydrosilyl)(methyl)amino-1-propyl]-1,2-cyclopentanedicarboximide, and N-[3-(diethylhydrosilyl)(methyl)amino-1-propyl]-1,2-cyclohexanedicarboximide.

10. The method of claim 4, where the imide compound is a N-[(1-aza-2-sila-1-cyclohydrocarbyl)hydrocarbyl]imide compound selected from the group consisting of N-[3-(2,2-dimethyl-1-aza-2-sila-1-cyclopentyl)-1-propyl]phthalimide, N-[3-(2,2-diphenyl-1-aza-2-sila-1-cyclopentyl)-1-propyl]maleimide, N-[3-(2,2-dimethyl-1-aza-2-sila-1-cyclopentyl)-1-propyl]citraconimide, N-[3-(2,2-diphenyl-1-aza-2-sila-1-cyclopentyl)-1-propyl]succinimide, N-[3-(2,2-diethyl-1-aza-2-sila-1-cyclopentyl)-1-propyl]-1,8-naphthalimide, N-[3-(2,2-diethyl-1-aza-2-sila-1-cyclopentyl)-1-propyl]-2,3-naphthalimide, N-[3-(2,2-dimethyl-1-aza-2-sila-1-cyclopentyl)-1-propyl]-1,2-cyclopentanedicarboximide, N-[3-(2,2-diethyl-1-aza-2-sila-1-cyclopentyl)-1-propyl]-1,2-cyclohexanedicarboximide, N-[3-(2,2-dimethyl-1-aza-2-sila-1-cyclohexyl)-1-propyl]phthalimide, N-[3-(2,2-diphenyl-1-aza-2-sila-1-cyclohexyl)-1-propyl]maleimide, N-[3-(2,2-dimethyl-1-aza-2-sila-1-cyclohexyl)-1-propyl]citraconimide, N-[3-(2,2-diphenyl-1-aza-2-sila-1-cyclohexyl)-1-propyl]succinimide, N-[3-(2,2-diethyl-1-aza-2-sila-1-cyclohexyl)-1-propyl]-1,8-naphthalimide, N-[3-(2,2-diethyl-1-aza-2-sila-1-cyclohexyl)-1-propyl]-2,3-naphthalimide, N-[3-(2,2-dimethyl-1-aza-2-sila-1-cyclohexyl)-1-propyl]-1,2-cyclopentanedicarboximide, and N-[3-(2,2-diethyl-1-aza-2-sila-1-cyclohexyl)-1-propyl]-1,2-cyclohexanedicarboximide.

11. The method of claim 4, where the imide compound is a N-(dihydrocarbylaminohydrocarbyl)imide compound selected from the group consisting of N-(3-dimethylamino-1-propyl)phthalimide, N-(3-diphenylamino-1-propyl)maleimide, N-(3-dimethylamino-1-propyl)citraconimide, N-(3-diphenylamino-1-propyl)succinimide, N-(3-diethylamino-1-propyl)-1,8-naphthalimide, N-(3-diethylamino-1-propyl)-2,3-naphthalimide, N-(3-dimethylamino-1-propyl)-1,2-cyclopentanedicarboximide, and N-(3-diethylamino-1-propyl)-1,2-cyclohexanedicarboximide.

12. The method of claim 4, where the imide compound is a N-[(1-aza-1-cyclohydrocarbyl)hydrocarbyl]imide compound selected from the group consisting of N-(3-pyrrolidinyl-1-propyl)phthalimide, N-(3-homopiperdinyl-1-propyl)maleimide, N-(3-pyrrolidinyl-1-propyl)citraconimide, N-(3-homopiperdinyl-1-propyl)succinimide, N-(3-piperidinyl-1-propyl)-1,8-naphthalimide, N-(3-piperidinyl-1-propyl)-2,3-naphthalimide, N-(3-pyrrolidinyl-1-propyl)-1,2-cyclopentanedicarboximide, N-(3-piperidinyl-1-propyl)-1,2-cyclohexanedicarboximide, N-[3-(4-methylpiperazinyl)-1-propyl]phthalimide, and N-[3-(4-methylhomopiperazinyl)-1-propyl]phthalimide.

13. The method of claim 1, where said step of reacting the chain ends occurs before the reactive polymer is quenched.

14. The method of claim 1, where said step of preparing the polymer includes polymerizing conjugated diene monomer and optionally monomer copolymerizable therewith.

15. The method of claim 1, where said step of preparing the polymer includes employing a coordination catalyst system.

16. The method of claim 15, where said coordination catalyst system includes a lanthanide-based catalyst system.

17. The method of claim 16, where the lanthanide-based catalyst system includes (a) a lanthanide compound, (b) an alkylating agent, and (c) a halogen-containing compound.

18. The method of claim 17, where the alkylating agent includes an aluminoxane and an organoaluminum compound represented by the formula $AlR_nX_{3-n}$, where each R, which may be the same or different, is a mono-valent organic group that is attached to the aluminum atom via a carbon atom, where each X, which may be the same or different, is a hydrogen atom, a halogen atom, a carboxylate group, an alkoxide group, or an aryloxide group, and where n is an integer of 1 to 3.

19. The method of claim 1, where said step of preparing the polymer takes place within a polymerization mixture including less than 20% by weight of organic solvent.

20. The method of claim 17, where the molar ratio of the imide compound containing a protected amino group to the lanthanide metal of the lanthanide compound is from about 1:1 to about 200:1.

21. The method of claim 1, where said step of preparing the polymer includes employing an anionic initiator.

22. The method of claim 21, where said anionic initiator includes an organolithium compound.

23. The method of claim 22, where said organolithium compound is selected from the group consisting of an alkyllithium compound, an aryllithium compound, a heterocyclic lithium compound, and a trialkyltinlithium compound.

24. A method for preparing a functional polymer, the method comprising the steps of:
(i) introducing conjugated diene monomer, optionally monomer copolymerizable therewith, and a catalyst or initiator to form a polymerization mixture; and
(ii) adding an imide compound to the polymerization mixture prior to quenching the polymerization mixture, where the imide compound is defined by one or more of the formulae:

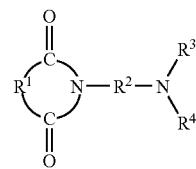

where $R^1$ and $R^2$ are each independently a divalent organic group, and $R^3$ and $R^4$ are each independently a mono-valent organic group or a hydrolyzable group, or R.sup.3 and R.sup.4 join to form a divalent organic group,

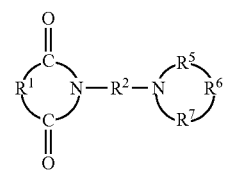

where $R^1$ and $R^2$, and $R^6$ are each independently a divalent organic group, and $R^5$ and $R^7$ are each independently a bond or a hydrolyzable group,

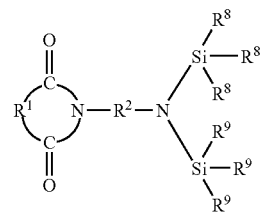

where $R^1$ and $R^2$ are each independently a divalent organic group, and $R^8$ and $R^9$ are each independently a hydrogen atom or a mono-valent organic group, or at least one $R^8$ and at least one $R^9$ join to form a divalent organic group, and

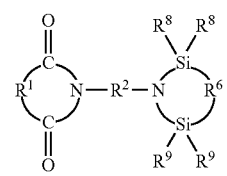

where $R^1$ and $R^2$, and $R^6$ are each independently a divalent organic group, and $R^8$ and $R^9$ are each independently a hydrogen atom or a mono-valent organic group.

* * * * *